(12) United States Patent
Ellenbogen

(10) Patent No.: US 7,427,138 B2
(45) Date of Patent: Sep. 23, 2008

(54) METHOD AND APPARATUS FOR IMPROVING VISUAL PERCEPTION

(75) Inventor: Nir Ellenbogen, Singapore (SG)

(73) Assignee: NeuroVision, Inc., Singapore (SG)

( * ) Notice: Subject to any disclaimer, the term of this patent is extended or adjusted under 35 U.S.C. 154(b) by 159 days.

(21) Appl. No.: 10/578,320

(22) PCT Filed: Nov. 4, 2004

(86) PCT No.: PCT/IL2004/001012

§ 371 (c)(1),
(2), (4) Date: May 4, 2006

(87) PCT Pub. No.: WO2005/044096

PCT Pub. Date: May 19, 2005

(65) Prior Publication Data

US 2007/0076168 A1    Apr. 5, 2007

Related U.S. Application Data

(60) Provisional application No. 60/517,095, filed on Nov. 5, 2003.

(51) Int. Cl.
*A61B 3/02* (2006.01)
*A61B 3/00* (2006.01)

(52) U.S. Cl. .................................... 351/243; 351/246
(58) Field of Classification Search .................. 351/44, 351/158, 246, 243; 382/128, 114
See application file for complete search history.

(56) References Cited

U.S. PATENT DOCUMENTS 4,950,167 A * 8/1990 Harris .......................... 434/322
6,876,758 B1 * 4/2005 Polat et al. ................... 382/128

* cited by examiner

*Primary Examiner*—Mohammed Hasan

(57) ABSTRACT

A method of improving the visual perception ability of a person by: displaying to the person in at least one evaluation sessions a plurality of images selected to test the visual perception ability of the person with respect to a visual defect, and to elicit responses from the person indicative of the level of the person's visual perception ability with respect thereto; and by utilizing the responses to select another plurality of images designed to treat the person with respect to a detected visual defect; applying training glasses with reduced refraction for the respective eye, and displaying to person another plurality of images in treatment sessions until the visual perception ability of the person has been improved.

20 Claims, 15 Drawing Sheets
(8 of 15 Drawing Sheet(s) Filed in Color)

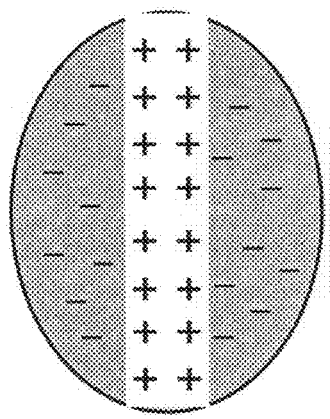 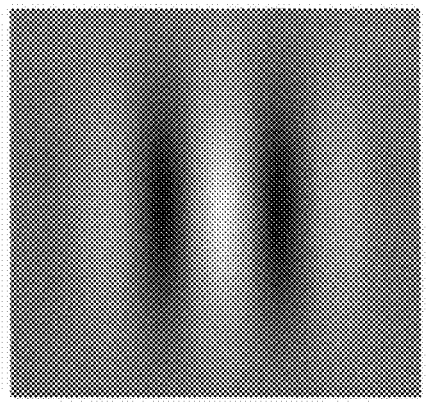
Fig. 1a
Prior Art
Fig. 1b
Prior Art
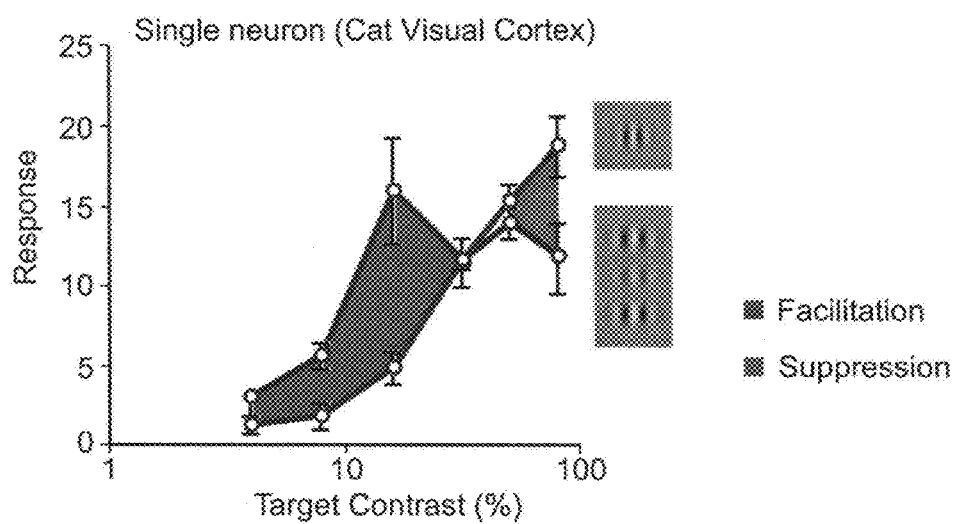
Fig. 2
Prior Art

METHOD AND APPARATUS FOR IMPROVING VISUAL PERCEPTION

RELATED APPLICATIONS

This application is a National Phase Application of PCT Patent Application Ser. No. PCT/IL2004/001012 having International Filing Date of Nov. 4, 2004, which claims the benefit of U.S. Provisional Patent Application No. 60/517,095 filed on Nov. 5, 2003. The contents of the above Applications are all incorporated herein by reference.

FIELD AND BACKGROUND OF THE INVENTION

The present invention relates to methods and apparatus for improving visual perceptions in accordance with the techniques described in the above-cited related applications. The following background will be helpful in understanding the improvements of the present invention.

SCIENTIFIC BACKGROUND

The visual system is a highly sophisticated optical processing mechanism, classically described as a hierarchy of visual processing stages (though recent views emphasize backward projections), starting from light detection and transduction in the eye (i.e. photoreceptors) through several stages of spatial integration, each stage forming receptive fields of increasing complexity.

Not all components imaged on the retina are equally perceived; some are constrained by the efficiency of neural processing in the brain. An important stage in image analysis in the primary visual cortex involves receptive fields (units) sensitive to image contrast that varies in a specific direction (orientation selectivity) on a specific scale (size selectivity). Human contrast sensitivity is best described by the aggregate response of these units (filters).

Cortical cells (neurons) are highly specialized and optimized as image analyzers, so they respond only to a limited range of parameters (filters) of the visual image, such as orientation, location in the visual field, and spatial frequency. Thus, to characterize an image, visual processing involves the cooperative activity of many neurons. These neural interactions contribute both excitation and inhibition. Spatial interactions between oriented receptive fields are an important factor in modulating activity of the corresponding neuronal units.

Contrast is one of the most important parameters activating cortical cells involved in vision processing. Responses of individual neurons to repeated presentations of the same stimulus are highly variable (noisy). Noise may impose a fundamental limit on the reliable detection and discrimination of visual signals by individual cortical neurons. Neural interactions determine the sensitivity for contrast at each spatial frequency, and the combination of neural activities set the Contrast Sensitivity Function (CSF). Theory suggests that the relationship between neuronal responses and perception are mainly determined by the signal-to-noise ratio (S/N ratio) of the neuronal activity. The brain pools responses across many neurons to average out noisy activity of single cells; thus improving the signal-to-noise ratio, leading to substantially improved visual performance.

In several studies, it has been shown that the noise of individual cortical neurons can be brought under experimental control by appropriate choice of stimulus conditions: Kasamatsu, T., Polat, U., Pettet, M. W. & Norcia, A. M. Colinear Facilitation Promotes Reliability of Single-cell Responses in Cat Striate Cortex. Exp Brain Res 138, 163-72. (2001); and Polat, U., Mizobe, K., Pettet, M. W., Kasamatsu, T. & Norcia, A. M. Collinear Stimuli Regulate Visual Responses Depending on Cell's Contrast Threshold. Nature 391, 580-4 (1998). Such studies also show that contrast sensitivity at low levels can be increased by a factor of 2 through control of stimulus parameters. At the neural level, the improvement in sensitivity would not be expected or largely reduced without a concurrent decrease in response noise. This precise control of stimulus conditions leading to increased neuronal efficiency is fundamental in initiating the neural modifications that are the basis for brain plasticity.

Brain plasticity relates to the ability of the nervous system to adapt to changed conditions, sometimes after injury or strokes, but more commonly in acquiring new skills. Brain plasticity has been demonstrated in many basic tasks, with evidence pointing to physical modifications in the adult cortex during repetitive performance. Several studies demonstrate the plasticity of neural interactions resulting from repetitive performance of specific visual tasks leading to improved visual performance. The improved visual functions, like skill learning, were retained after a few years of retesting. Both an increased range of excitatory interactions and reduced inhibition were observed in subjects with normal vision, and in monkeys. These studies point to activity-dependent plasticity of the visual cortex, where the specific connections activated throughout repetitive performance are modified, leading to improved performance.

The technology in the above-cited related applications probes specific neuronal interactions, using a set of patient-specific stimuli that improve neuronal efficiency and induce improvement of CSF due to a reduction of noise and increase in signal strength—followed by a marked improvement in spatial resolution (Visual Acuity).

"Lateral Masking": Modulation of CSF

The typical building block of the the visual stimulations is the Gabor patch (FIGS. 1a and 1b). "Gabor Patches" are widely used in the field of visual neuroscience. They have been shown to efficiently describe and match the shape of receptive fields of neurons in the primary visual cortex and thus represent the most effective stimulation.

The set of Gabor functions is defined as a collection of odd (sine) and even (cosine) wave functions with limited spatial extent (and/or temporal extent).

$$Go(x,y)=Aoexp(-((x-xo)2+(y-yo)2)/o2)*\sin(2\pi/\lambda*(x\cdot\cos(\theta)+y\cdot\sin(\theta)))$$

Contrast response of a single neuron can be modulated by activity of neighboring neurons, as shown by single-unit recordings of neuronal activity in the visual cortex of cats and monkeys.

Recent research by Polat, U., Mizobe, K., Pettet, M. W., Kasamatsu, T. & Norcia, A. M., conducted invasively, utilizing cat subjects, demonstrated the linear relationship between contrast and neuronal response (green line) as shown in FIG. 2. Research published in Nature in 1998 revealed a non-linear response to the same target when surrounded by flanking images (blue line). These flanking images where found to increase response (facilitation) at lower contrast levels and decrease response (suppression) at higher contrast levels. This fundamental discovery regarding the neural connections responsible for vision in cats is also fundamental to the techniques involved in the present invention for vision improvement in humans.

It has been demonstrated that contrast sensitivity of adult human subjects at low levels can be significantly increased through specific control of the Gabor patches parameters. This stimulation-control technique, where collinearly-oriented flanking Gabors are displayed in addition to the target gabor image, is called "Lateral Masking".

The results shown in FIGS. 3 and 4 are derived from subjects (adults) with normal vision, who were exposed to psychophysical tasks using the lateral masking technique:

When subjects practice contrast modulation under a very precise and subject-specific stimuli regimen, a dramatic improvement in contrast sensitivity is achieved.

About Amblyopia

Amblyopia is defined as reduced visual acuity in an eye that cannot be cured or improved by refractive correction, while eye pathology does not exist. It is a developmental abnormality of the central nervous system that leads to impaired vision. It is caused during early childhood, when one of the eyes is crossed and/or significantly unfocused. When the difference between the two images sent from the eyes to the brain is such that the brain cannot fuse both the images to a single one, the "weak" eye's image is drastically suppressed by the brain to avoid double or blurry vision. Amblyopia is a common public health problem that affects 2%-4% of the population in the industrial world.

The visual function of the amblyopic eye is dramatically reduced. Amblyopic visual acuity is defined as less than 20/30, but can be as bad as the "legally blind" level (20/200) and sometimes even worse. According to the NIH/NEI Visual Acuity Impairment Study (VAIS), amblyopia is the leading cause of monocular vision loss in the 20 to 70+ age group, surpassing diabetic retinopathy, glaucoma, macular degeneration and cataract.

Patients with amblyopia substantially use only one eye, and do not have three-dimensional (stereoscopic) vision. Naturally, their spatial orientation is impaired and they have reduced peripheral vision. They are at increased risk of blindness if vision for any reason is lost in their good eye. Amblyopia may also lead to restrictions in educational and occupational opportunities, and may also affect a person's lifestyle. A Quality of Life study conducted among adult amblyopes demonstrates the extent of these influences.

Ideally, amblyopia is diagnosed by a pediatrician when a child is quite young. Treatment by a pediatric ophthalmologist has the potential to correct the condition by the time the child is three or four years of age. However, to treat this condition, a young child must wear an eye patch that covers the good eye for an extended period of time. A significant number of children find patches uncomfortable or socially embarrassing, and have a natural aversion to having their only good eye covered. The result is poor compliance, which leads to ineffective treatment. Lack of compliance, combined with late detection and unsuccessful treatment, result in a significant number of children reaching adulthood (the critical age of nine and above) suffering from the condition.

Amblyopia is considered treatable only in children younger than nine years of age, primarily by occluding the good eye and forcing the "lazy eye" to function. It is considered untreatable in individuals older than nine years, an age that is referred to as the "critical age".

About Myopia

Myopia is defined as a refractive condition in which rays of light entering the eye parallel to the optic axis are brought to a focus in front of the retina. It can be also referred as a refractive condition where the farthest point of focus is located at a point near to the observer, and not at infinity, thus Myopia is often referred as Near-sightedness or Shortsightedness. When one is nearsighted, distance vision is blurred at all times while near vision is often excellent within a certain range.

There are a number of causes of this optical condition. The eyeball may be too long, causing the image to be focused short of the retina at the back of the eye. Or, the focusing lenses of the eye are too strong.

Eyeglasses and contact lenses are the safest and most practical optical remedies. The lens power, whether it be in spectacles or contact lenses, is a minus power, which cancels the excessive plus power of near-sightedness. The image now comes to a clear focus at the back of the eye, on the retina.

Myopia often occurs combined with Astigmatism. Astigmatism is distorted vision caused by a warpage in the optics of the eye. As shown in FIG. 11a, the image presented to the retina at the back of the eye is out of focus only for light waves entering at a certain angle, along a certain meridian. As shown in FIG. 11b, astigmatism is generally corrected by a lens (spectacle or contact lens) which is astigmatic opposite to that of the eye. Such a lens is called a toric or cylinder lens.

OBJECTS AND BRIEF SUMMARY OF THE PRESENT INVENTION

An object of the present invention is to provide a method and apparatus for improving visual perception with respect to various types of eye conditions generally, but particularly with respect to amblyopia, presbyopia and myopia, with or without astigmatism.

According to one aspect of the present invention, there is provided a method of improving the visual perception ability of a person with respect to a particular eye condition of at least one eye, comprising: in at least one evaluation session of an evaluation phase, displaying to the person a plurality of images selected to test the visual perception ability of the person with respect to at least one visual defect, and to elicit responses from the person indicative of the level of the person's visual perception ability with respect to the at least one visual defect; utilizing the responses to select another plurality of images designed to treat the person with respect to a detected visual defect and thereby to improve the visual perception ability of the person with respect to the detected visual defect; and in a treatment phase, applying to the at least one eye of the person, training glasses with reduced refraction for the respective eye; and displaying to the person the another plurality of images in at least one treatment session while the training glasses are applied to the at least one eve of the person. until the visual perception ability of the person has been improved with respect to the detected visual defect.

According to another aspect of the present invention, there is provided apparatus for improving the visual perception ability of a person with respect to a particular eye condition of at least one eye, comprising: a display device for displaying images to the person: an input device for displaying images to the person; training glasses to be worn by the person and having a reduced refraction with respect to at least one eye of the person; and a processor programmed such that: in an evaluation phase, before the training glasses have been applied to the person, the processor controls the display device to display to the person a plurality of images selected to test the visual perception ability of the person with respect to at least one visual defect, and utilizes responses inputted by the person via the input device to select another plurality of images designed to improve the visual perception ability of the person with respect to a detected visual defect: and in treatment phase, after the training glasses have been applied to the person, the processor controls the display device to display to the person the another plurality of images to thereby improve the visual perception ability of the person with respect to the detected visual defect.

According to the preferred embodiments of the invention described below, the treatment phase includes a plurality of treatment sessions in each of which are displayed to the person a plurality of images designed to elicit responses to be used for selecting the plurality of images in a subsequent treatment session such as to progressively improve the visual perception ability of the person with respect to the detected visual defect. After at least one treatment session, the refraction of the training glasses is increased, decreased, or remains the same for the next treatment session as determined in order to progressively improve the visual perception ability of the person with respect to the detected visual defect. At least one predetermined parameter of the plurality of images displayed in one treatment session is varied in the subsequent treatment session.

More particularly, in the described preferred embodiment, the treatment phase includes a plurality of treatment sessions each of which includes a plurality of visual perception tasks. In each such task there is displayed to the person at least one image including stimuli designed to elicit a response useful for selecting at least one other image to be displayed in the subsequent visual perception task of the respective treatment session such as to progressively improve the visual perception ability of the person with respect to the detected defect.

In one described preferred embodiment, the visual perception tasks in at least some of the sessions in the treatment phase include spatial frequency changes in which the spatial frequency of the stimuli is changed. As described, the spatial frequency is changed starting with lower spatial frequencies and progressively moving to higher spatial frequencies.

In another described preferred embodiment, in at least some of the sessions in the treatment phase, the orientation of the stimuli is changed. The described preferred embodiment is one wherein the eye condition includes astigmatism characterized by a distortion area in an astigmatic zone; and wherein, in at least some of the treatment sessions in the treatment phase, the orientations of the stimuli are changed by progressing towards the distortion area in the astigmatic zone.

In all the described preferred embodiments, the treatment phase includes a sufficient number of treatment sessions to improve the person's sensitivity contrast function by the person achieving a desired range of contrast levels.

The invention is described below in a system wherein the plurality of images are displayed in a client's terminal in both the evaluation phase and the treatment phase; and wherein the elicited responses are communicated to a remotely-located server and utilized to select the another plurality of images designed to treat the person with respect to the detected visual defect.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1a-4 are diagrams referred to in the above description of the background;

FIG. 5 is a series of diagrams illustrating various manipulations of visual stimuli that may be involved in a treatment according to the present invention;

FIG. 6 is a diagram illustrating the reduced CSF (Contrast Sensitivity Function) in amblyopic patients;

FIG. 7 is a diagram illustrating abnormal lateral interactions is amblyopic patients;

FIG. 8 is a diagram illustrating visual acuity improvement in patients treating according to the present invention;

FIG. 9 is a diagram illustrating visual acuity improvement during the treatment phase and improvement subsequently;

FIG. 10 is a diagram illustrating contrast sensitivity function improvement during the treatment phase and improvement subsequently;

FIGS. 11a and 11b are diagrams illustrating myopic and astigmatic eye conditions, respectively;

FIG. 12 is a diagram illustrating reduced CSF in myopic patients;

FIG. 13 is a diagram illustrating enhancing lateral interactions in myopic patients treated in accordance with the present invention;

FIG. 14 illustrates improvements in uncorrected visual acuity of patients treated in accordance with the present invention;

Figure 15:
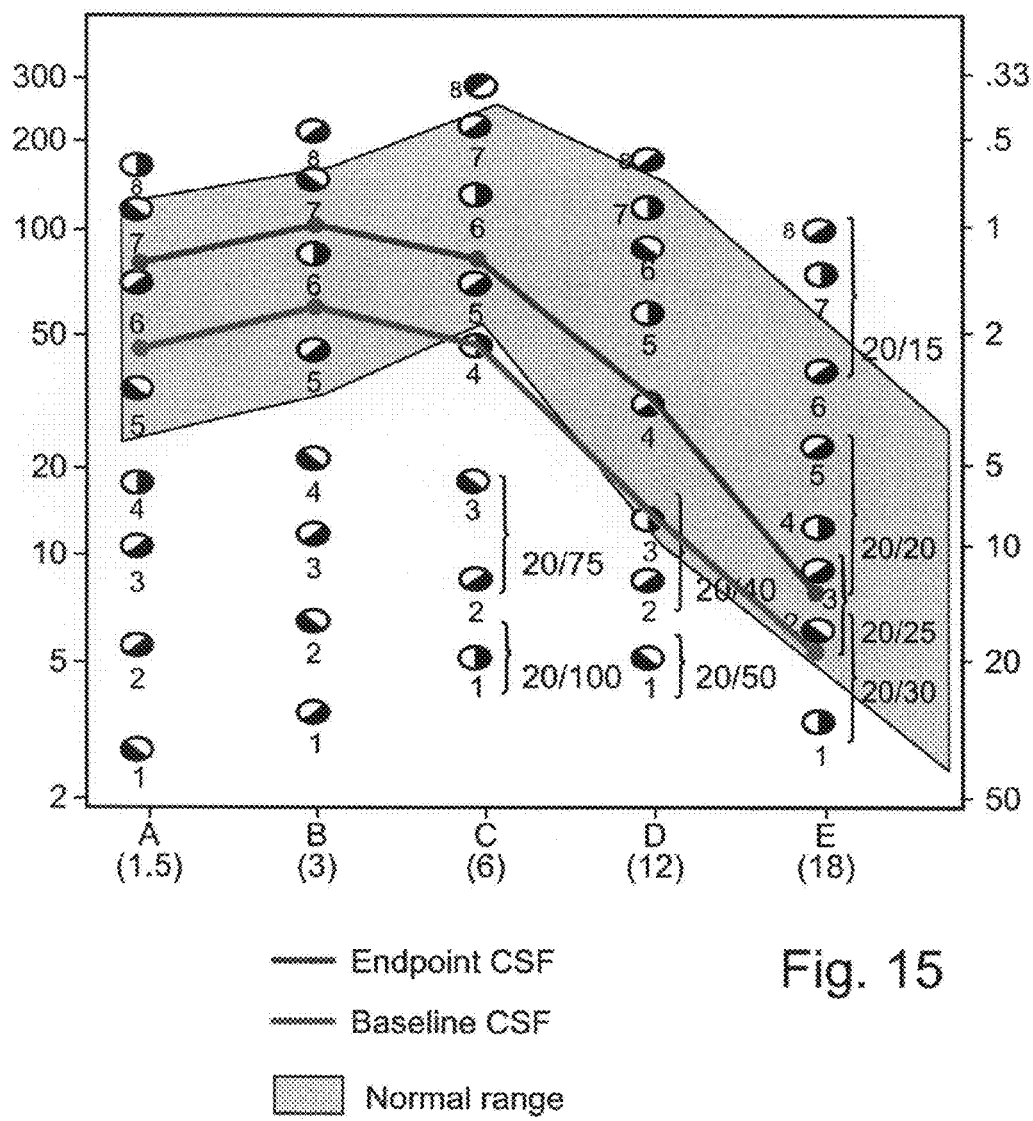
Figure 16:
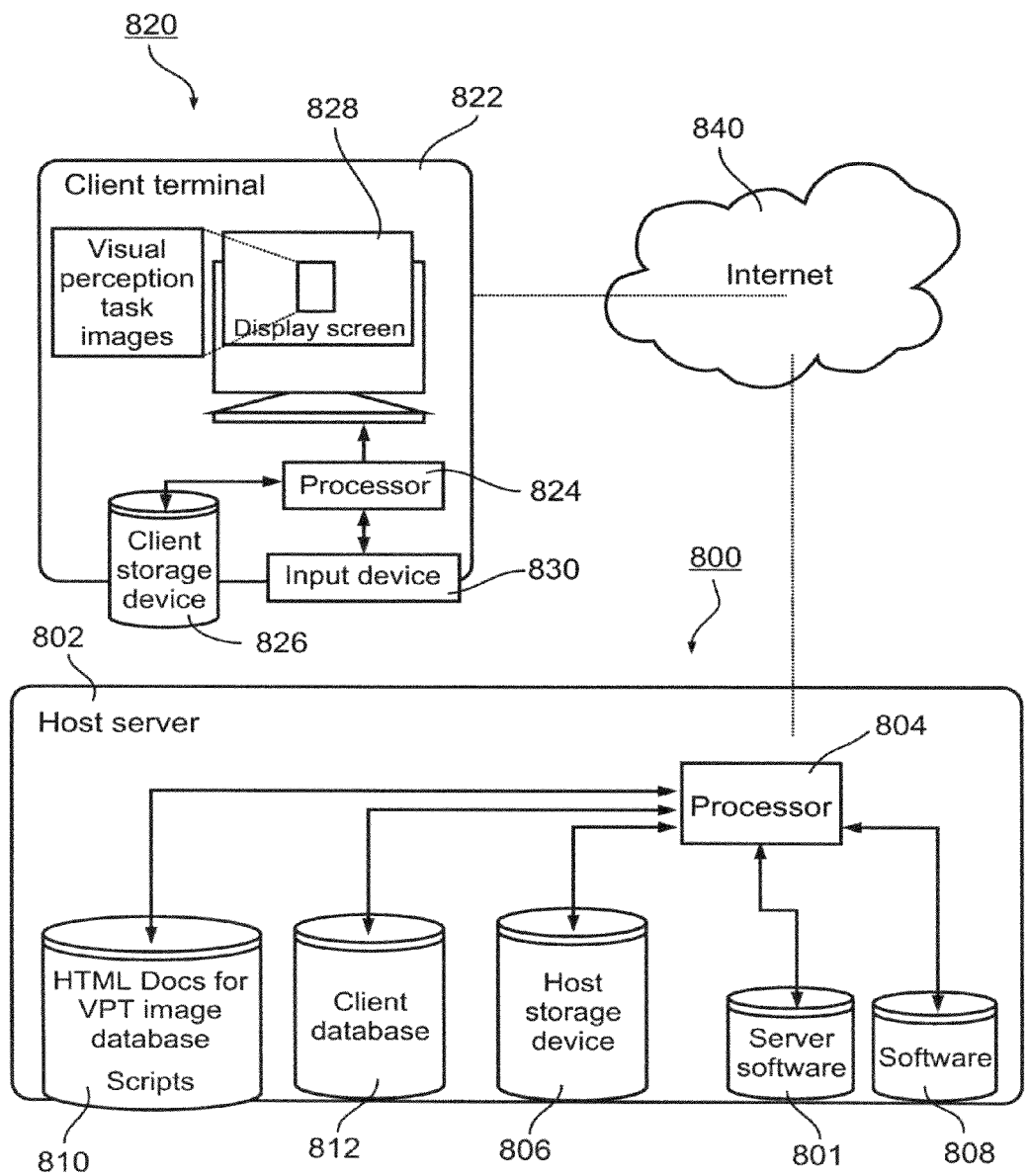
Figure 17:
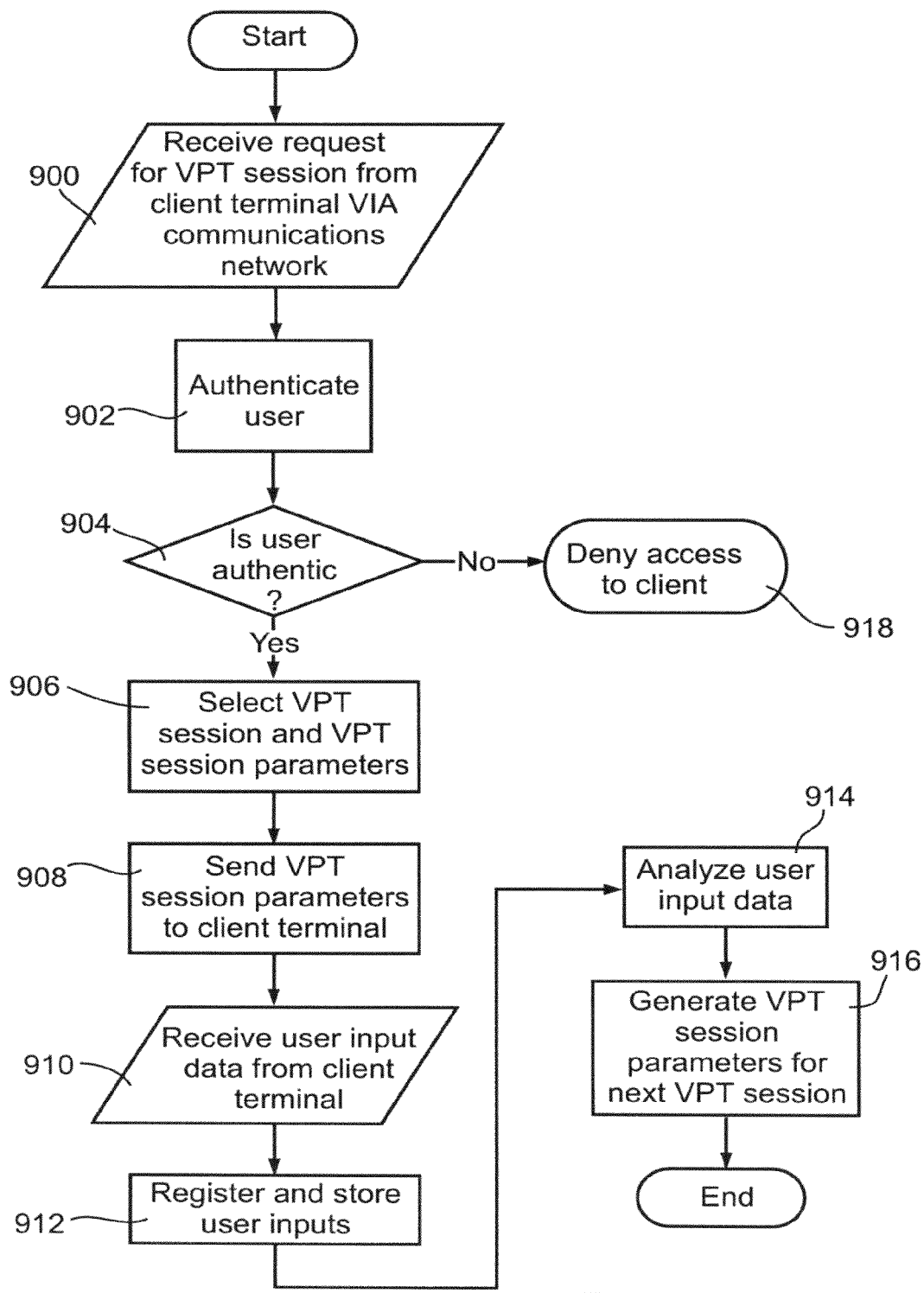
Figure 18:
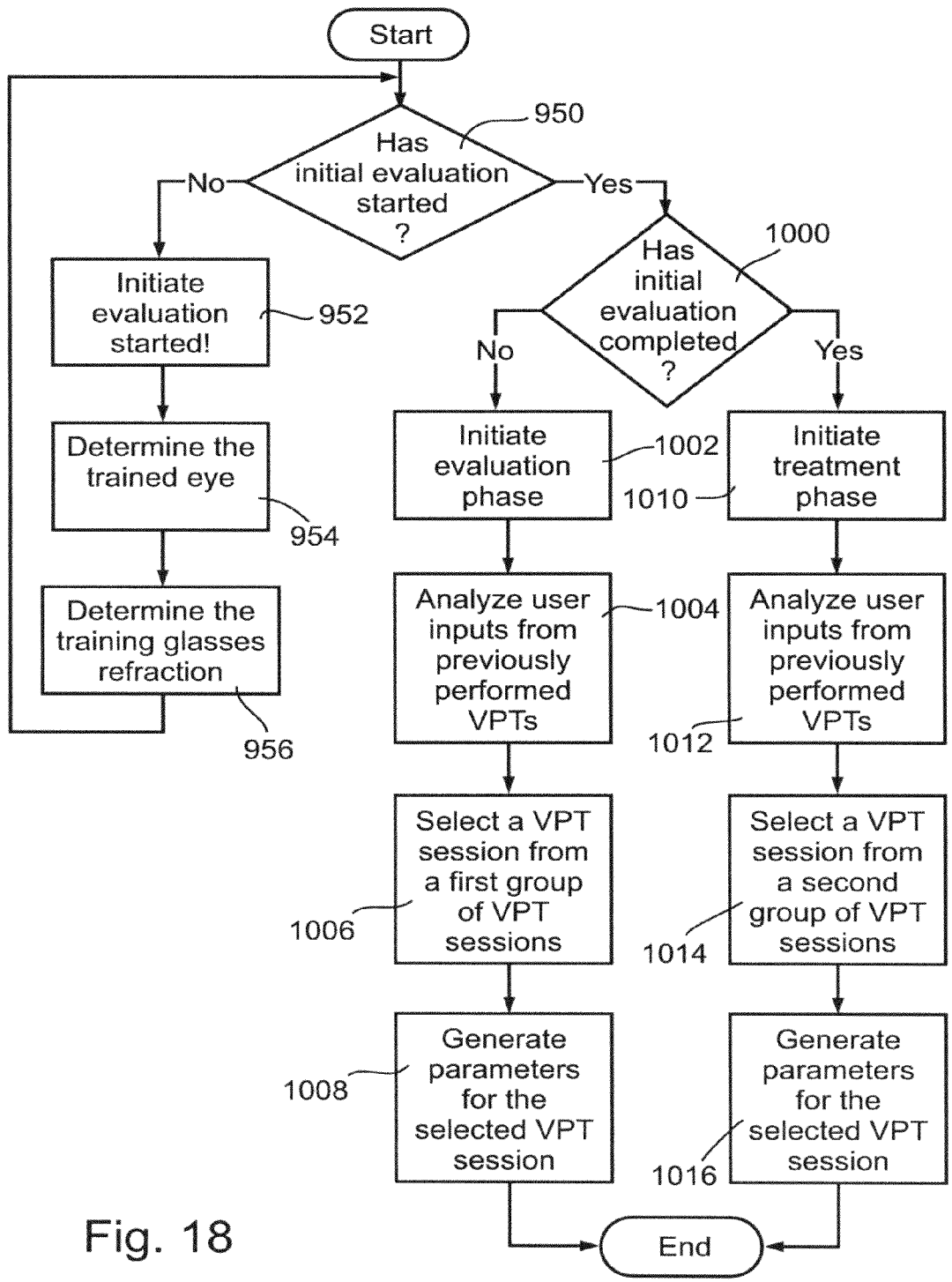
Figure 19:
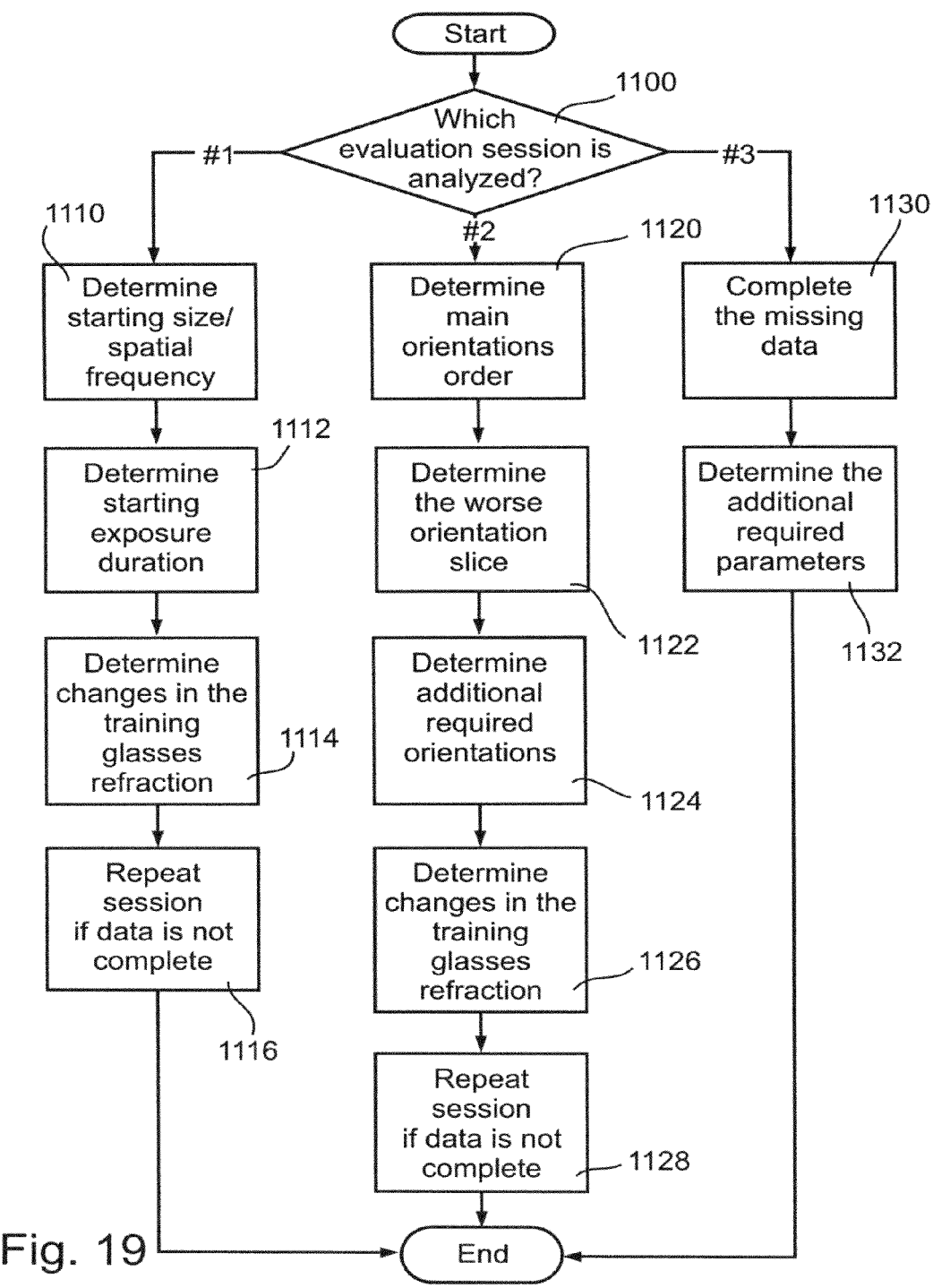
Figure 20:
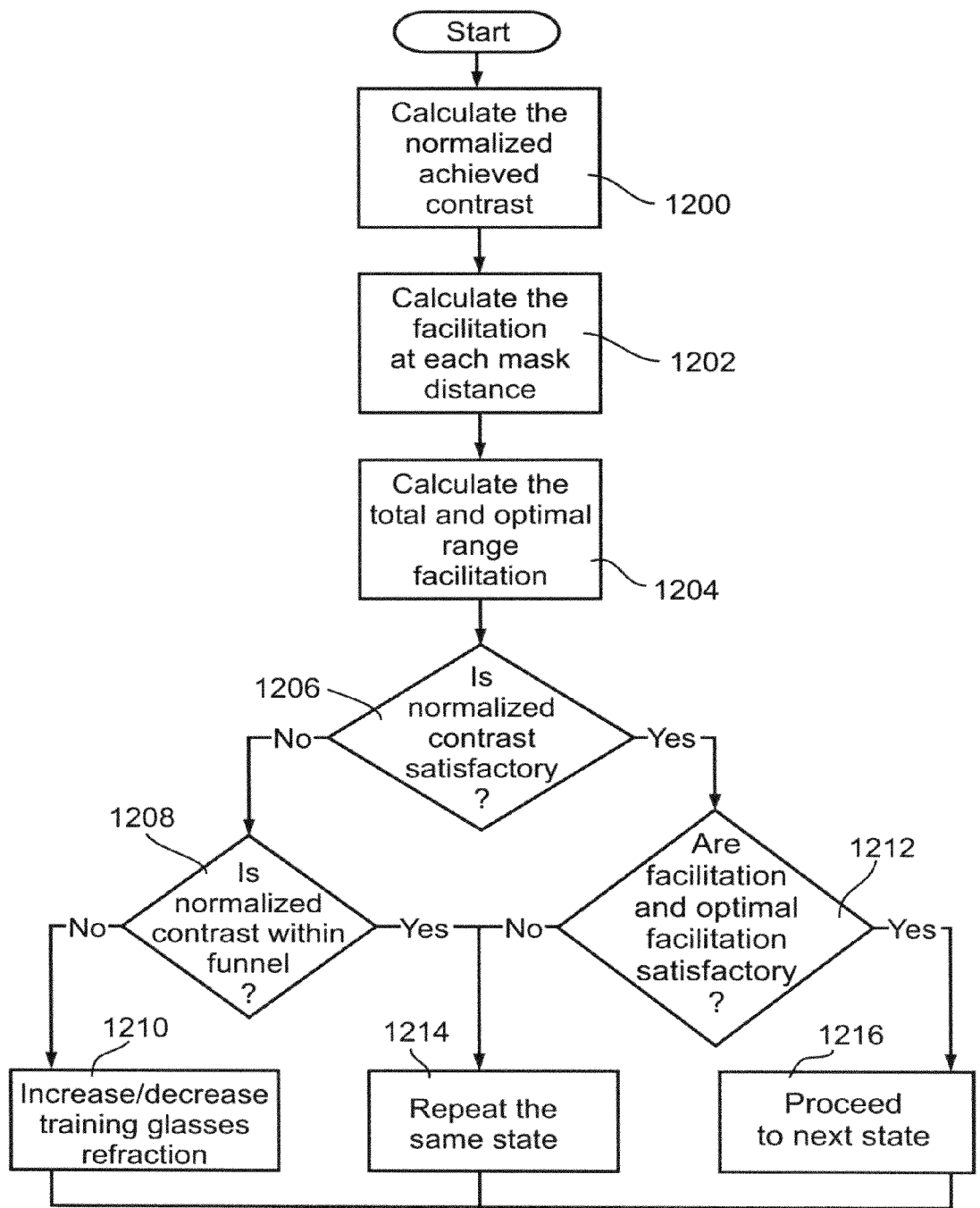
Figure 21:
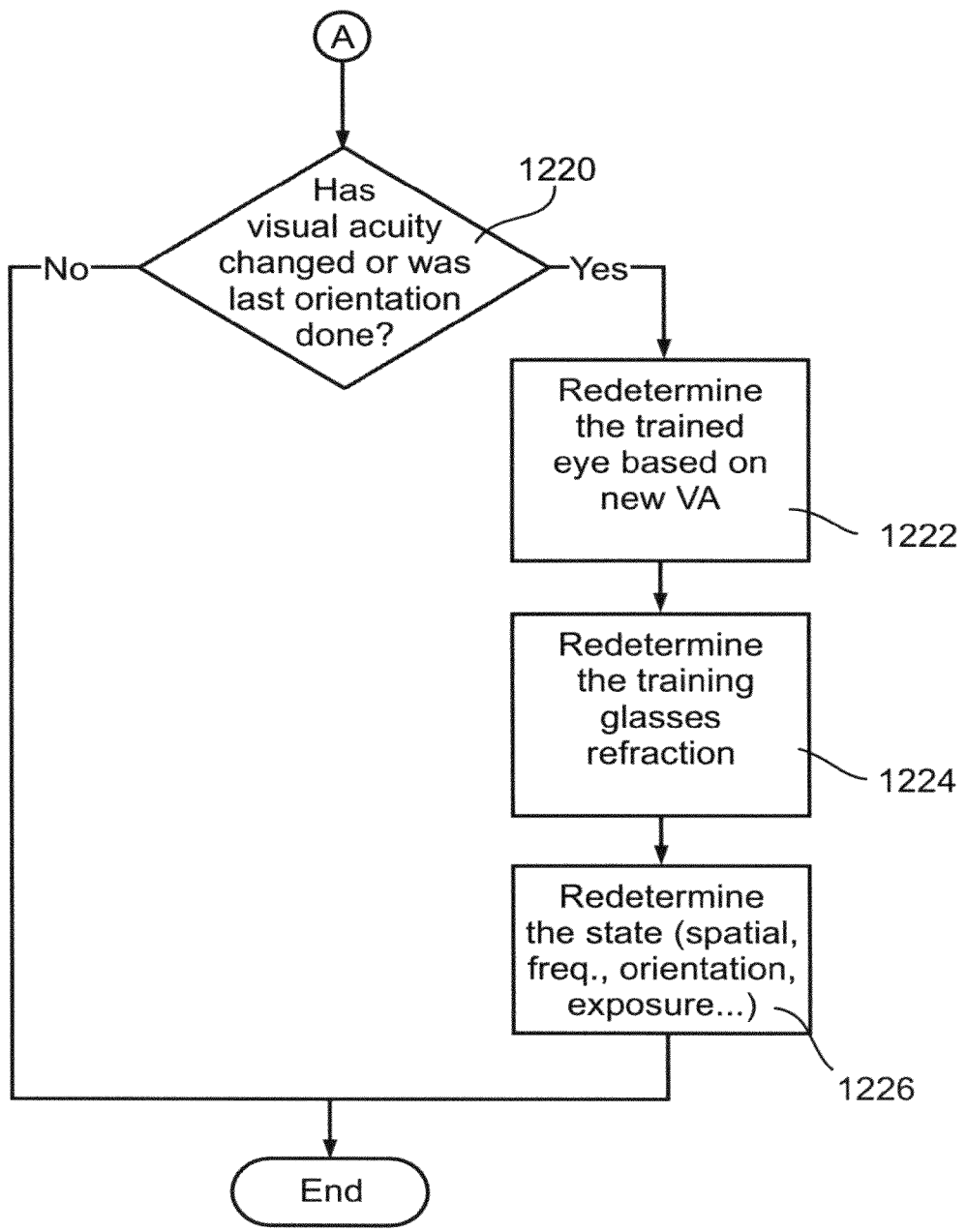

FIG. 15 is a diagram illustrating improvements in CSF during the treatment phase in accordance with the present invention;

FIG. 16 is a block diagram illustrating the architecture of one system constructed in accordance with the present invention;

FIG. 17 is a flow chart illustrating the operations performed by the server side in a treatment session cycle;

FIG. 18 is a flow chart illustrating the operations performed by the server side in a selected VPT (visual perception task) session;

FIG. 19 is a flow chart illustrating the analysis of an evaluation sessions; and FIGS. 20 and 21 are flow charts illustrating the analysis of treatment sessions.

DESCRIPTION OF PREFERRED EMBODIMENTS

Treatment Concept—Overview

As will be described more particularly below, the present invention involves a computerized interactive treatment in which the patient is exposed to a series of psychophysical visual tasks—"Visual Perception Tasks (VPT)". A VPT aims to measure or improve a person's visual perception process. In fact, each VPT is generally designed to target a specific aspect of the visual perception process.

The various VPT's implemented by the system have structuring for performing all the following operations:

א. Providing a patient with visual stimuli designed to stimulate one or more areas of the patient's visual cortex;

ב. Receiving responses to the visual stimuli from the patient using an input device (e.g., the computer mouse); and then ג. Providing more visual stimuli based on responses to the previous visual stimuli, until a threshold level is reached.

The treatment is administered in successive 30-minute sessions, each session comprised of a series of VPT's., 2-3 times a week for a total of approximately 30 sessions.

As each patient suffers from individual specific neural capabilities, the treatment is personalized—specifically tailored to each individual subject. Subject specificity is achieved by the following measures:

1. Analysis and identification of each subject's neural deficiencies or inefficiencies or within normative range capabilities through performance of a set of visual perception tasks to which the subject is exposed. This stage is called the computerized evaluation stage, and is usually comprised of up to three sessions. As a result, a treatment plan is defined.

2. Based on said analysis, administering patient-specific stimuli in a controlled environment. The visual stimuli parameters are algorithmically controlled and tailored to each subject's needs in order to address and improve the identified neural deficiencies or inefficiencies or enhance the neuronal activity beyond the normative range. This is the treatment stage and is usually comprised of approximately 30 to 50 treatment sessions, depending on each individual performance.

Each treatment session is designed to train, directly and selectively, those functions in the visual cortex that were diagnosed to be potentially enhanced. During each session an algorithm analyzes the patient's responses and accordingly adjusts the level of visual difficulty to the range most effective for further improvement.

Between sessions, the performance and progress of the patient are measured and taken into account by the algorithm for the definition of the visual stimuli parameters of the next therapeutic session. Thus, for each subject an individual training schedule is designed based on the initial state of visual performance, severity of dysfunction and progress in therapeutic training.

The visual stimuli parameters are algorithmically controlled and tailored to each subject's needs. Among these parameters are: Spatial Frequencies, Spatial arrangement of the Gabor patches, Contrast level, Orientation (local and global), Tasks Order, Context and Exposure Timing.

The foregoing treatment may be used to improve vision of subjects with several eye conditions, including but not limited to: (1) Amblyopia, (2) Myopia, (with or without Astigmatism) (3) Presbyopia, (4) Hyperopia, (5) Emmetropia, (for obtaining super-normal vision) (6) Ammetropic post refractive surgery patients, (being left with residual refractive errors), and (8) Eye diseases causing reduced vision, such as glaucoma or age-related macular degeneration (AMD). It may also be used to reduce progression of myopia in childhood.

The invention is particularly useful for treating amblyopia and myopia (with or without astigmatism), and is therefore described below with respect to such treatments.

Amblyopia Treatment Principles

Amblyopia, as mentioned above, is defined as reduced visual acuity in an eye that cannot be cured or improved by refractive correction. Even when using the best refractive correction, Amblyopes are characterized by several functional abnormalities in spatial vision, including: reduced Visual Acuity, reduced Contrast Sensitivity Function (CSF), and impaired contour detection. The reduction in CSF, which is mainly pronounced at high spatial frequencies, is believed to result from a low S/N (signal-to-noise) ratio. A low S/N ratio is shown to limit performance on letter identification.

The reasons Amblyopes suffer from these functional abnormalities that can not be remedied through the use of corrective lenses or surgery are defects in the neurological component of a person's visual perception process. Amblyopes suffer from abnormal neural interactions and reduced excitation and increased inhibition, an effect that underlies deficient contrast response, and crowding effect.

Figure 3:
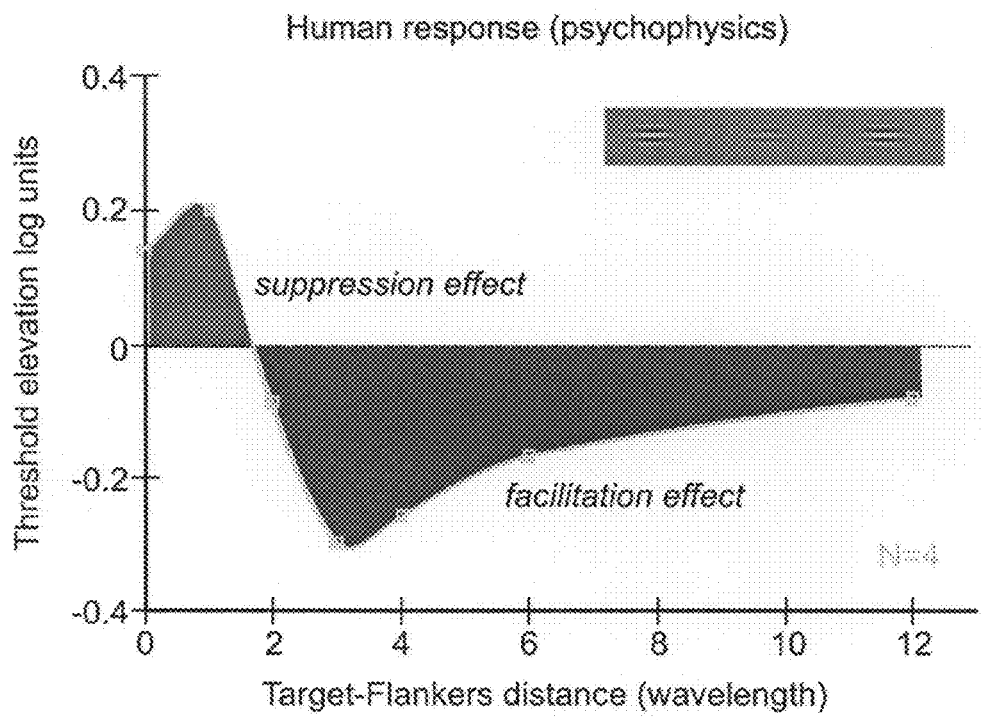
Figure 4:
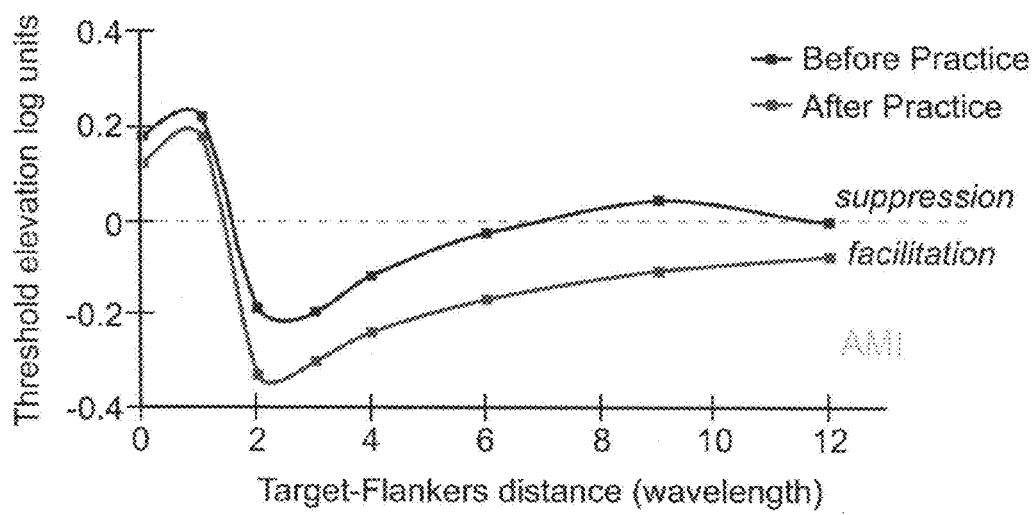
Figure 5:
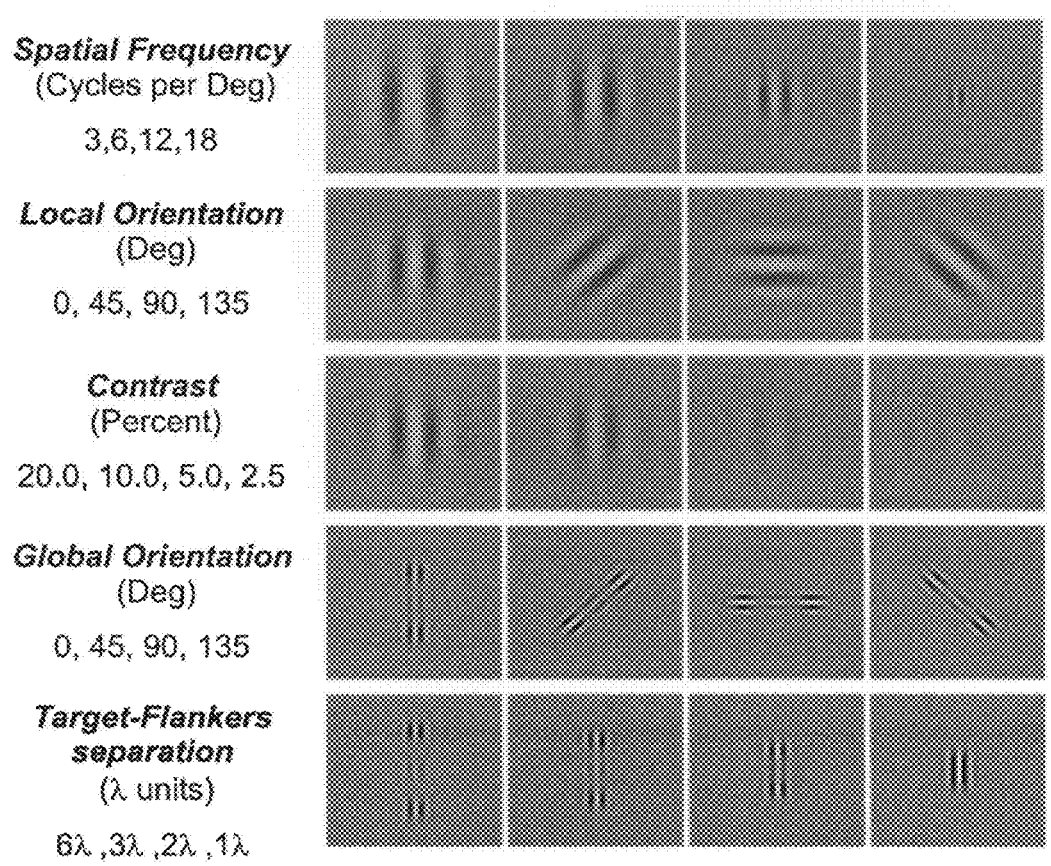
Figure 6:
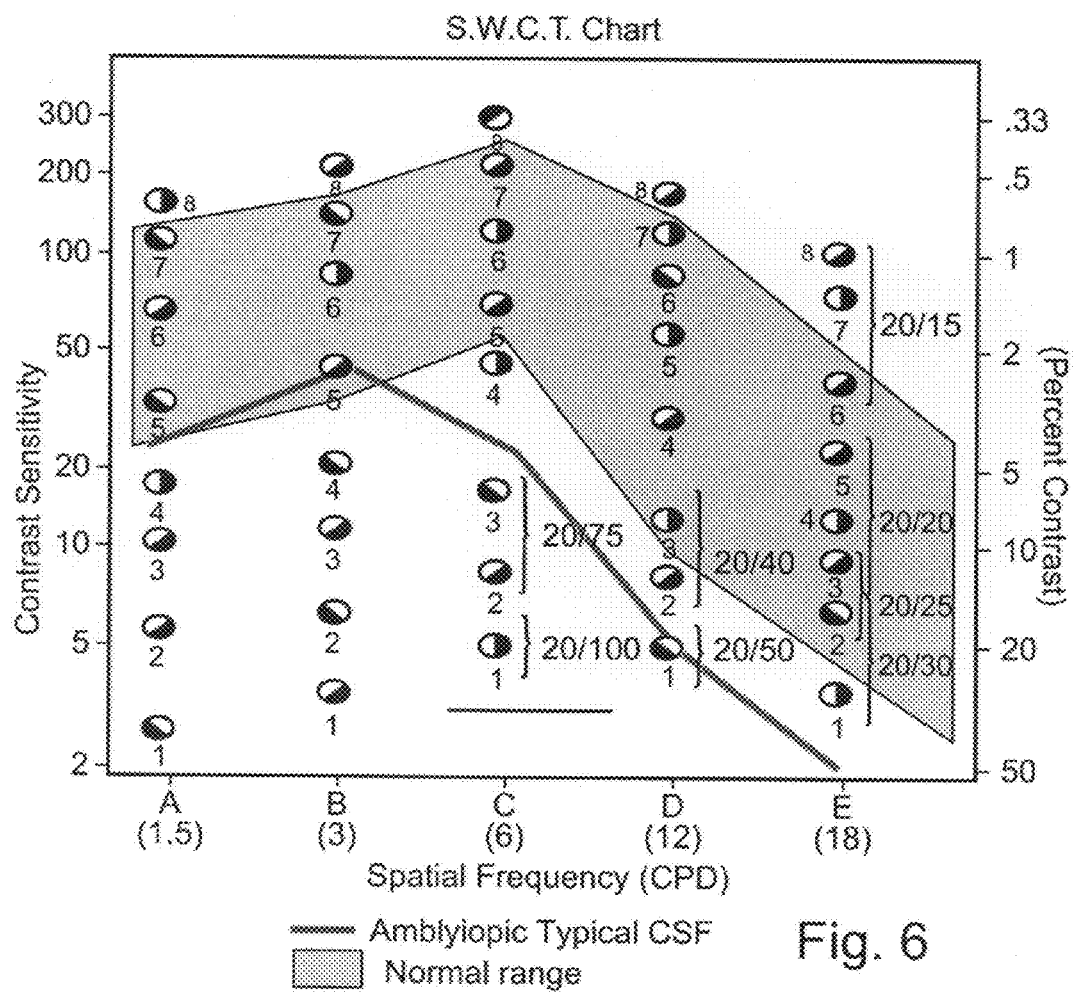
Figure 7:
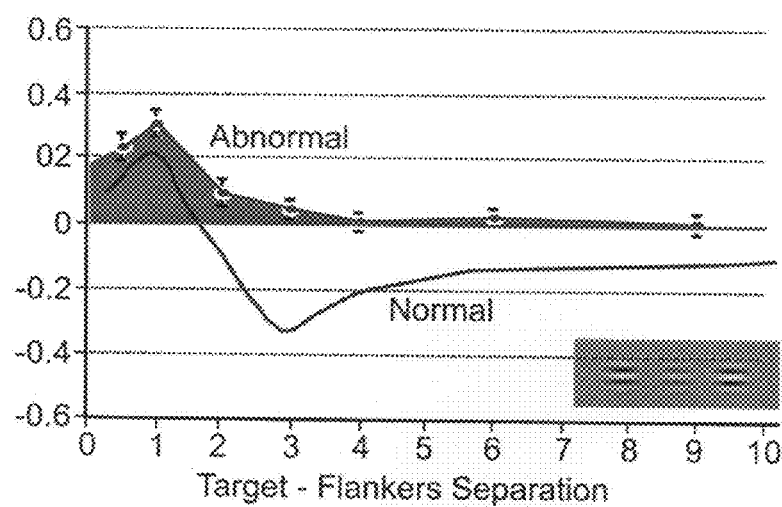

FIG. 7 presents the abnormal "Lateral Masking" graph resulting from those abnormal neural interactions compared to a normative "Lateral Masking" graph.

The Amblyopia treatment aims to improve the deficient lateral interactions, increase the S/N ratio, and improve the impaired contour integration and spatial localization.

This is mainly achieved through Visual Perception Tasks (VPTs) focusing in reduction of the lateral inhibition. Practicing the lateral interactions leads to an increased range of those interactions.

Through the personalized treatment sessions, the size (spatial-frequency) and orientation of the stimuli are changed, starting with lower spatial-frequencies and progressively moving to the higher ones, with four orientations at each size.

The trained spatial frequencies are selected according to the level of abnormality, which is measured during the computerized evaluation. Amblyopes often suffer from subnormal contrast sensitivity in mid to high special frequencies.

For optimal improvement, the achieved contrast thresholds should enter into a contrast funnel. If contrast exceeds this funnel, the Gabor patches are elongated towards the local orientation axis, in order to decrease contrast thresholds.

Meridional Amblyopia, which means unequal contrast response at various orientations despite optimal refractive correction, is addressed by changing the orientation, starting with the easier one (at which lower contrasts are achieved) and progressively moving to the harder one.

The zone of suppression receives high attention, as abnormal lateral interactions are expressed in increased suppression. The VPTs initially concentrate at the area of low suppression level. Upon improvement, and creation of a certain level of facilitation, the focus will gradually shift to the area of higher suppression level, which will follow to improve as well.

The Amblyopia treatment also aims to improve the spatial localization. This is achieved through practicing of alignment displacement VPTs. The treatment is uniocular; the amblyopic eye is trained, while the fellow eye is occluded with a semi-translucent lens.

The treatment is performed using the best refractive correction for the Amblyopic eye. The best refractive correction should be also used in all daily activities. If major refraction difference exists between the eyes, contact lenses only should be used, to avoid projection of different image sizes from the eyes to the brain.

The above described NVC (neural vision correction) treatment principles have been proven in the clinical treatment of amblyopia, a condition where the visual system is underdeveloped due to abnormal visual input to the brain during the critical period (up to age nine). The treatment has been tested in controlled randomized placebo clinical trials on adults (aged nine to 55) having baseline vision between 20/30 and 20/100 in their amblyopic eye. The trials were performed under the auspice of the Sheba Medical Center in Israel. Certified external auditors routinely monitored the trials for GCP compliance.

The Clinical Trial Success Criteria Were as Follows:
1. Best Corrected Visual Acuity (BCVA) improvement of a minimum of two lines in ETDRS chart of over baseline, in a minimum of 60% of completed subjects.
2. Maintenance of the improved visual acuity (+/−50%) after three months post-treatment.

The Following are the Clinical Study Results Highlights:
1. The success rate within the treatment group (44 patients) was 70.5% (31 out of 44 patients).
2. The average improvement among all 44 patients (including patients that did not show improvement) was 2.5 ETDRS lines.
3. The control group showed no improvement.
4. Average improvement within the sub-group that was successfully treated (70% of the patients) was 3.1 lines, which is a doubling of the visual acuity.
5. Almost half of the successfully treated sub-group reached 20/25 vision or better, while 19% (6 patients) improved to 20/20 vision or better ("super-normal vision").
6. Among patients having a baseline VA of 20/50 and worse, 70% achieved a final VA of 20/40 and better.
7. The contrast sensitivity function (CSF) of the treatment group improved remarkably and significantly. The CSF average—after treatment was within the normal range.
8. Additional visual functions, i.e. binocular functions and reading abilities (near visual acuity), were significantly improved among the treatment group.
9. Retention monitoring at 12 months post treatment showed excellent results.

Figure 8:
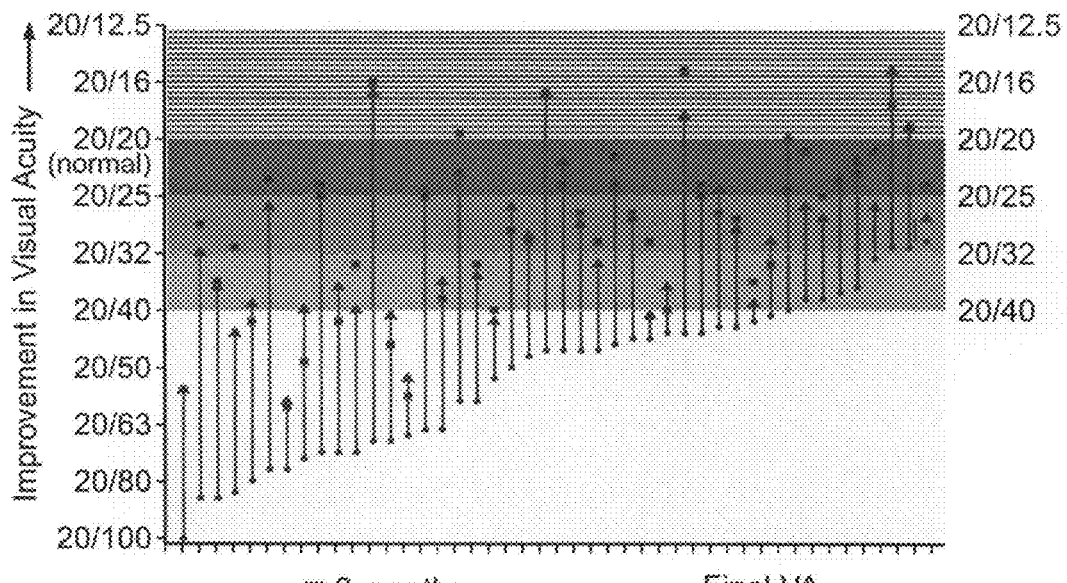
Figure 9:
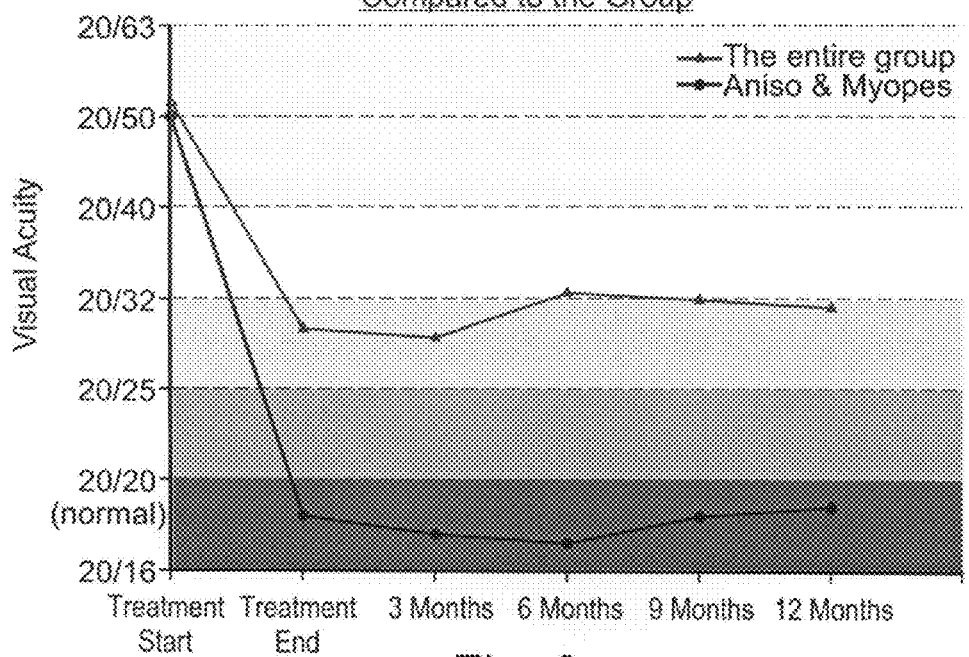
Figure 10:
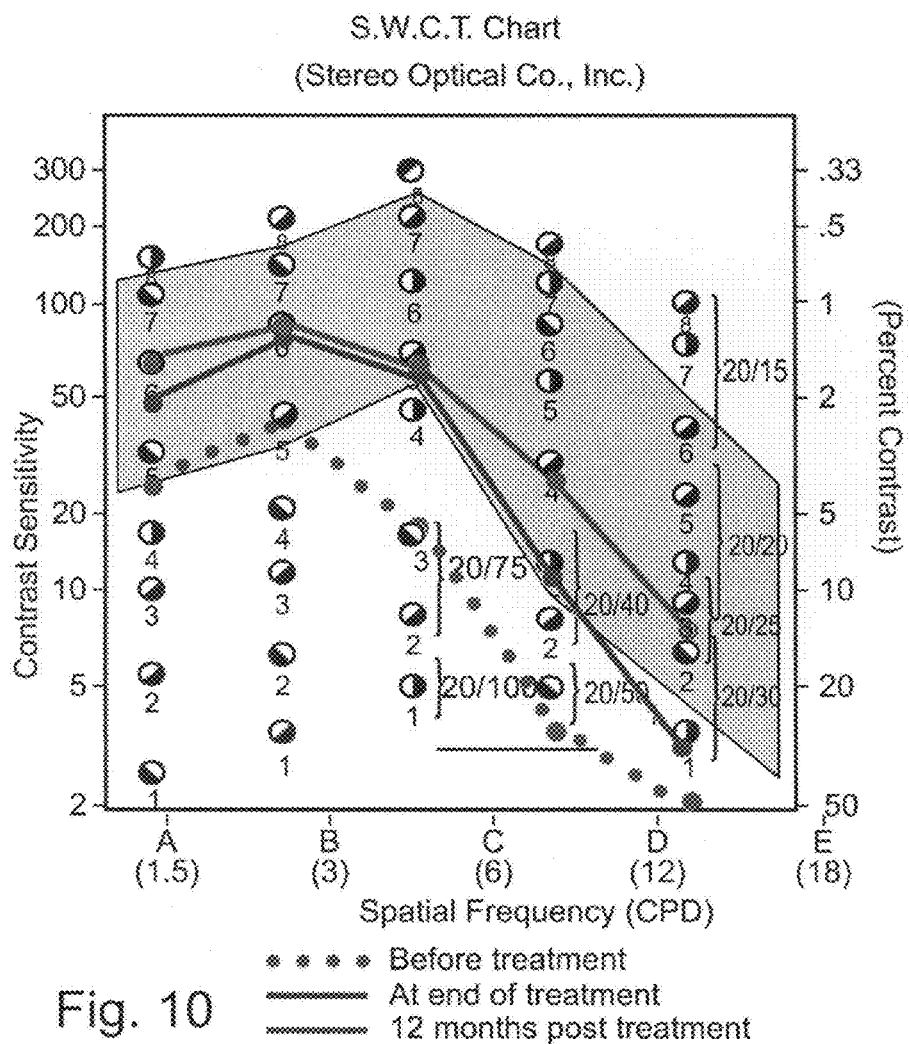
Figure 11A:
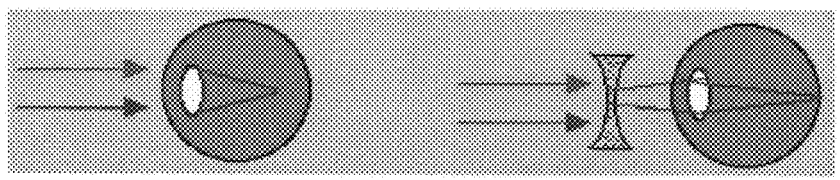
Figure 11B:
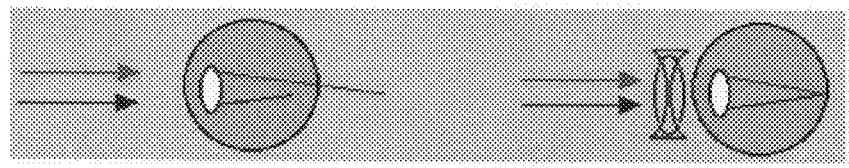

FIG. 8 presents the individual Visual Acuity improvement of all treatment group patients. FIG. 9 presents the treatment group average Visual Acuity improvement during the treatment phase and the retention of this improvement one year post treatment. FIG. 10 presents the treatment group average Contrast Sensitivity Function improvement during the treatment phase and the retention of this improvement one year post treatment.

NVC Second Generation Applications

The first-generation application (the Amblyopia treatment discussed above) dealt with a visual condition where the "back end" of the visual system—the neurological component—is deficient; however the "front end" of the visual system—the ocular or the optical component—is optimal by nature or by using corrective lenses. The visual perception is limited by the defective or sub normal neurological component. The aim of that treatment is to improve the functionality of the deficient neural system as close as possible to normative level in order to improve vision.

The second-generation applications deal with a different situation, namely with subjects having sub-optimal ocular conditions; however their neuronal connectivity is developed normally and is capable of processing images relatively efficiently. In those visual conditions the visual input is subnormal and limited by the ocular "front end" of the visual system.

The aim of this treatment is to further enhance the neurological component functionality beyond the normative range in order to improve the neuronal S/N ratio, which leads to improved contrast sensitivity, and thereby to improved visual acuity. Improving one's contrast sensitivity function simply means improving its ability to see more sharply.

The ability to improve contrast sensitivity by enhancing the efficiency of the neural processing makes the treatment also applicable to improving visual acuity under disparate conditions, such as Myopia, Presbyopia, Hyperopia. Other possible applications include residual refractive errors in Post-refractive surgery subjects and other eye diseases causing reduced vision, such as glaucoma or age-related macular degeneration (AMD).

Another possible application is in reducing the progression of myopia in children. This condition appears to be directly linked to visual images presented during the early years of life. Animal models of myopia have clearly established that a blurred visual image (either from occluding the eye, or from inducing refractive errors with lenses) directly results in abnormal eye growth, often resulting in an extremely elongated eyeball, resulting in high myopia. It therefore follows that if visual perception can be enhanced or sharpened in a developing myopic eye in childhood, there is a possibility that this may break the positive feedback loop, and myopia progression may be reduced significantly.

Myopia Treatment Principles

Figure 12:
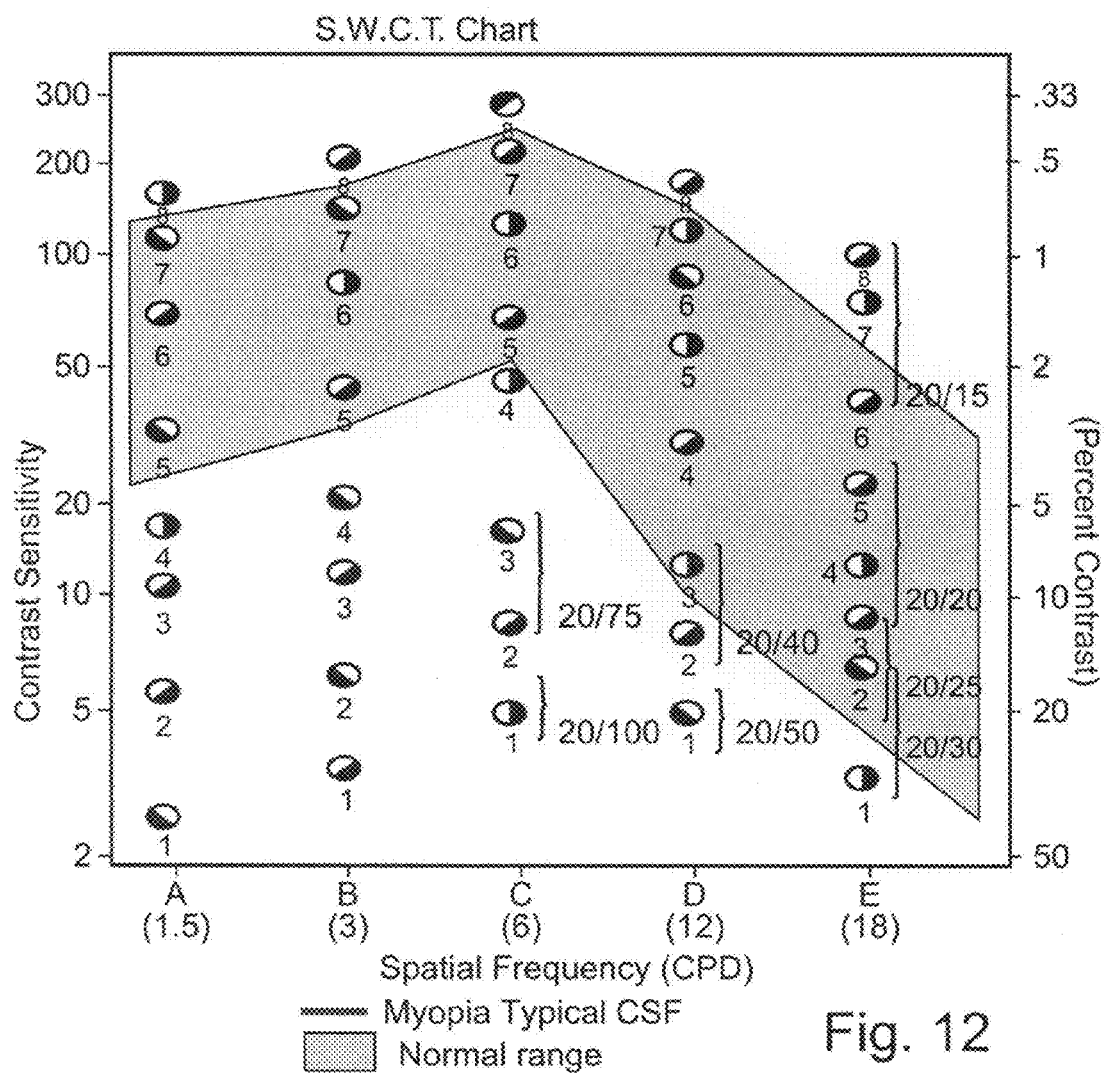

In Myopia, the neuronal connectivity is developed normally and is capable of processing images relatively efficiently; however the visual input is subnormal and limited by optics. The visibility of mid and high spatial frequencies is perceived as low contrast even when their physical contrast is high. Thus, CSF is reduced at the high spatial frequencies, resembling the amblyopic CSF, which as a consequence, degrades visual acuity (VA). FIG. 12 illustrates the reduced uncorrected CSF in myopic patients.

Activation of neurons in the visual cortex is directly related to signal strength (contrast). When the effective contrast is low, neurons are weakly activated, resulting in low S/N ratio at the respective spatial frequencies. A low S/N ratio is shown to limit performance on letter identification.

As blurred vision results from sub-optimal activity of the neurons vis-á-vis current optics, the Low Myopia treatment aims to improve the S/N (Signal to Noise) ratio, further improve the lateral interactions, and enhance the CSF in particular at Mid-High spatial frequencies.

This is mainly achieved through Visual Perception Tasks (VPTs) focusing in increasing of the lateral excitations.

Increasing Facilitation

Figure 13:
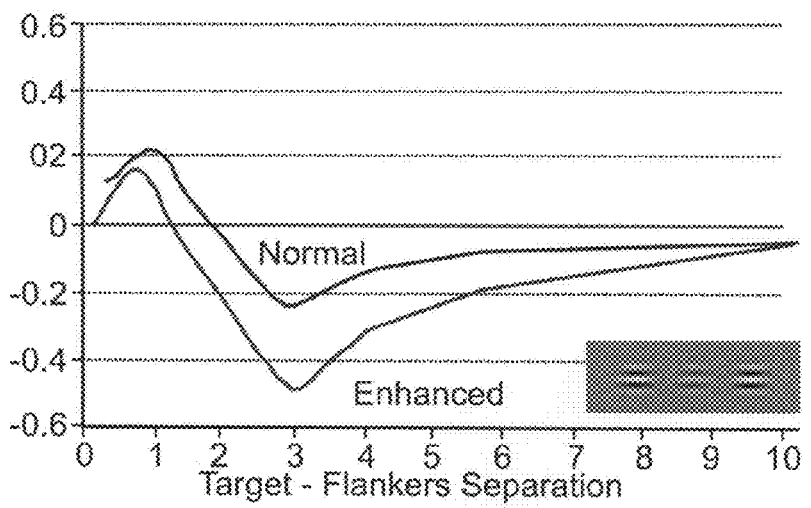

The zone of facilitation receives high attention. Practicing the lateral interactions leads to an increased range of those interactions. Treatment focuses in increasing the facilitation level at Target-Flankers separation distance of 2-4 wavelengths. Visual perception tasks at the said Target-Flankers separation distances are repeated to allow further perceptual learning. FIG. 13 illustrates enhancing lateral interactions in myopic patients.

The Trained Eye

The treatment is either binocular or uniocular. A decision is taken according to the uncorrected visual acuity of both eyes and the respective best corrective refraction. This decision is re-evaluated in the course of treatment. The preference is to train binocularly. However when the normalized uncorrected visual ability difference between the eyes exceeds the limit that allows binocularity, then the stronger eye will only be active by default. Therefore, in such cases, when aiming to train the weaker eye, the stronger eye will be covered with a semi-translucent lens and the weaker eye is trained uniocularly.

The Trained Eye Might Change in the Course of Treatment:
1. From binocular to uniocular in case of visual acuity changes that increase the visual acuity difference between the eyes to the extent that justifies training the weaker eye.

2. From uniocular to binocular in case that the visual acuity difference between the eyes has decreased to a limit that allows binocularity or when vision improvement in the weaker eye has exhausted.
3. From uniocular to uniocular—mainly in the case of relatively high astigmatism.

Training Glasses with Reduced Refractive Correction

For optimal improvement, the achieved contrast thresholds at any configuration (spatial frequency, orientation, exposure duration) should enter into a contrast funnel. As Myopes suffer from blurred distance vision (when uncorrected or under corrected), many patients might exceed the effective contrast funnel for various spatial frequencies and orientations.

In order to keep the contrasts within the required range, the patients are preferably provided with training glasses with reduced refractive correction.

The refraction value of the training glasses is determined according to the training eye decision (left, right or both eyes), the uncorrected visual acuity in the respective eyes and patient's refraction. This decision may be changed in the course of treatment based on the achieved contrast levels.

The provided training glasses refraction would be any value between zero and the subject's best refractive correction at, but not limited to the interval of 0.5 diopter (D). For example a subject with refractive error of −1.75D might be given training glasses of −1.5D or −1.0D or −0.5D or no refraction at all.

Spatial Frequency

Through the personalized treatment sessions, the size (spatial-frequency) of the stimuli is changed, starting with lower spatial-frequencies and progressively moving to the higher ones.

The trained spatial frequencies are selected according to the level of subnormality, which is measured during the computerized evaluation. Myopes often suffer from subnormal contrast sensitivity in mid to high special frequencies, when using partial refraction correction or when uncorrected.

Repetitions of the same spatial frequencies are applied in order to stabilize the achieved perceptual learning, and in accordance to performance.

Spatial frequency also depends on the eye swap management. For example, when swapping from binocular to uniocular training, high spatial frequencies would be reduced to lower spatial frequencies.

Orientation

At each spatial frequency the patient is trained at various orientations. Whereas in the first generation application the subject is trained using the best refractive correction such that optical astigmatism is neutralized, here the trained orientations are selected according to the level of meridional subnormality.

If no astigmatism exists, the trained orientations would be 0, 45, 90 and 135 degrees. However in the presence of astigmatism, the astigmatic zone is gradually approached, starting with easier orientations and progressing towards the distortion area. At each spatial frequency, six orientations or even more may be involved. For example, a subject with astigmatism at 90 degrees might be trained in the following order: 0, 135, 45, 60, 75, 90, or 0, 45, 135, 105, 75, 90, or similar.

Low Myopia Treatment Clinical Results

Test have been conducted according to the above-described second-generation applications in the treatment of subjects having Low Myopia or low degrees of refractive errors. Low Myopia is defined as spherical refraction up to −1.5DS (Spheric Diopter) and astigmatism up to −0.5DC (Cylinder Diopter).

Low myopia affects over 100 million worldwide. The prevalence of low myopia is higher among the Chinese population. In Singapore, Hong Kong and Taiwan, over 80% of the population are myopic, and over 30% of the population fall within the Low Myopia definition.

The efficacy of the low myopia treatment has been proven in two pre-clinical studies. The treatment has been tested on adults (aged 17 to 55) having spherical equivalence $\leq 1.50DS$ of myopia in their worst eye, and $\leq 0.50DC$ of astigmatism in either eye, and Uncorrected VA baseline vision $\leq 20/100$ in their worst eye.

The Clinical Trial Success Criteria are as Follows:
1. For Baseline UCVA<=20/32, end UCVA<=20/20.
2. For Baseline 20/32<UCVA<=20/63, end UCVA<= (Baseline-2 ETDRS lines).
3. For Baseline 20/63<UCVA<=20/100, end UCVA<=20/40. in a minimum of 60% of completed subjects.

The Following are the Highlights of the Study Results:
1. The success rate was 79.5% (27 out of 34 eyes).
2. The average visual acuity improvement was 2.7 ETDRS lines.
3. 55% of the treated eyes reached 20/25 vision or better, while 35% improved to 20/20 vision or better ("supernormal vision").
4. The contrast sensitivity function (CSF) improved remarkably and significantly. The uncorrected CSF average—after treatment was well within the normal range.

Figure 14:
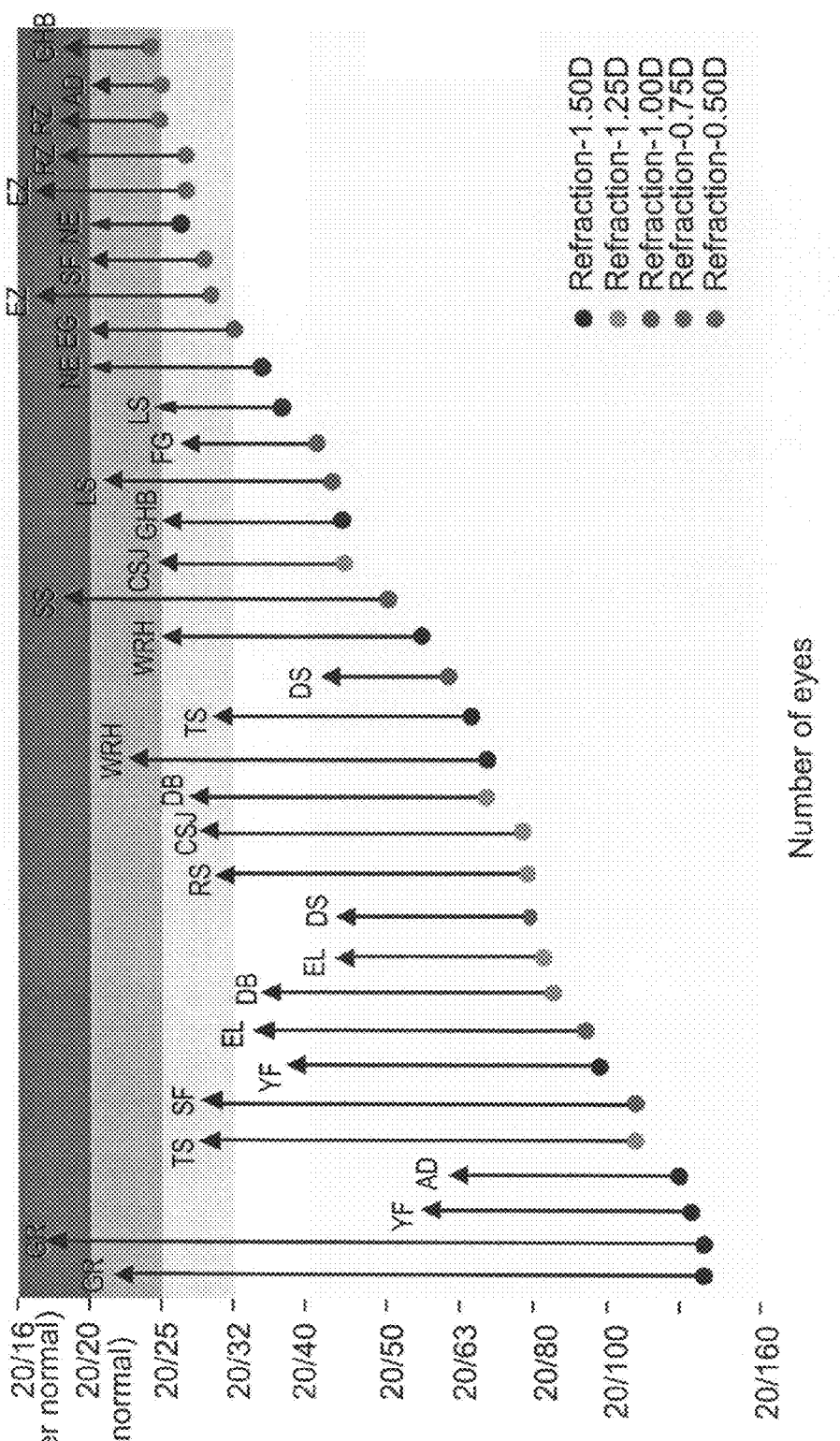

FIG. 14 presents the individual Uncorrected Visual Acuity improvement of all treated eyes. FIG. 15 presents the treatment group average CSF (contrast sensitivity function) improvement during the treatment phase.

Following are the main differences between the First and Second Generation Applications:

| Subject | Second Generation | First Generation |
|---|---|---|
| Deficient visual perception component | Ocular component | Neurological component |
| Eye Swap Management | Exists. Trained eye might be Left, Right or Both eyes. Changes as the treatment progresses | Does not exist. Only Amblyopic eye trained |
| Training Glasses Management | Exists Training glasses with reduced refraction are used. Refraction may change as the treatment progresses | Does not exist Best Refractive correction for Amblyopic eye during the entire treatment. |
| Inter-dependency between trained eye, training glasses refraction and VPT spatial frequency | Exists Spatial frequency changes in accordance with the change in trained eye or the change in training glasses refraction | Does not exist |
| Lateral Masking VPT focus | Increasing Facilitation | Reducing Suppression |
| Spatial Localization VPT | Does not Exist | Exists |

-continued

| Subject | Second Generation | First Generation |
|---|---|---|
| Effective Contrast Funnel maintained through | Training glasses management | Gabor patches elongation and increase in exposure duration. |
| Orientation Selection | Up to six or more orientations, depending on Astigmatism level and axis. | Four main orientations: 0, 45, 90, 135 |

Contrast Funnel

The term "Contrast Funnel" refers to the desired range of contrast levels a patient is expected to achieve in order to gain optimal vision improvement while undergoing NeuroVision treatment.

This range of contrasts (defined as Minimum contrast and Maximum contrast) depends on a series of parameters:
1. The patient's eye condition that we are aiming to improve
2. The normative values—the values a subject with normal vision would achieve in a similar task
3. The VPT spatial frequency
4. The VPT orientation
5. The VPT exposure duration
6. The training glasses used
7. The training mode—Binocular or Uniocular For example, the optimal contrast ranges for diagonal orientations are higher than those for vertical and horizontal orientations.

The treatment algorithms would adjust the treatment sessions parameters in order to allow the individual patient achieve the desired contrast levels within the funnel.

A Preferred Hardware and Software Implementation

FIGS. 16-21 illustrate a preferred hardware and software implementation of the invention as described above.

The hardware implementation illustrated in FIG. 16 includes a host server 800 and a client terminal 820. Host server 800 is typically a computer system 802 on a network with server software 801 configured to receive and answer requests for information. Typically, computer system 802 is also dedicated to storing data files and managing network resources, including network traffic. Computer system 802 generally includes a processor 804 and a data storage device 806, and is typically connected to a global communication network, such as the Internet 840.

Host server 800, through processor 804, has access to software 808 comprising sequences of instructions that cause processor 804 to perform a number of acts in accordance with the preferred methods described herein. Host server 800 also has access to a client database 812 that stores information concerning persons of the system. This information can include identification information and data relating to a person's performance during past VPT Sessions. Client database 812 may reside outside host server 800, such as at client terminal 820.

Client terminal 820 is a remote terminal that provides an interface for a person to access host server 800. Client terminal 820 is typically a computer system 822 communicatively coupled to host server 800 by a communication network, such as the Internet 840. Computer system 822 generally includes a processor 824, a data storage device 826, a display screen 828, an input device 830, and software comprising sequences of instructions that cause processor 824 to perform a number of acts in accordance with the methods described herein.

FIG. 17 is a flowchart depicting a preferred implementation of how the method is carried out at host server 800. Starting with step 900, host server 800 first receives a request from client terminal 820 for access to a VPT Session. This request is sent from client terminal 820 to host server 800 over a communication network, such as the Internet 840.

In step 902, an authentication routine is performed to determine whether the request from client terminal 820 is valid. Generally, host server 800 does this by sending a request over the Internet to client terminal 820 for a username and password. In step 904, upon receiving the username and password data from client terminal 820, host server 800 compares that data to username and password data stored in client database 812. If host server 800 determines that the person is authentic, the process continues to step 906. If the person is deemed to be non-authentic, a message is sent to client terminal 820 informing the person that access to the VPT Sessions is denied, as shown in step 918. At that point, the person may be allowed to re-enter his or her username and password information a number of times.

In step 906, after host server 800 determines that the username and password supplied are genuine, a VPT Session is selected and an initial set of VPT Session parameters are generated. Typically, these parameters are defined in advance. The VPT Session is selected according to the methods described below, and the VPT Session parameters are generated as explained below with reference to step 916. The VPT Session parameters define items such as contrast level, contours, spatial frequency, distance between objects, target placement, local and/or global orientations, and presentation time for each of the VPTs and VPT Images 100 being used to test or improve the visual perception process of a person.

In step 908, the initial VPT Session parameters are delivered to client terminal 820 over the Internet 840. Software resident on client terminal 820 is configured to receive the VPT Session parameters and use them to dynamically generate VPT Images 100 and VPTs. Once the parameters are delivered, the VPT Session can be carried out solely at client terminal 820 without the need for further interaction with host server 800. This preferred configuration allows the VPT Session to be administered to the person without delay or interruption.

In step 910, after the VPT Session has been administered to the person, host server 800 receives a set of person performance data from client terminal 820. The person performance data is data relating to the person's performance, which primarily comprises the stabilized values generated for each series of VPTs administered during a VPT Session. It can also include some or all of the user inputs received by client terminal 820. The person performance data is generated by client terminal 820 and is then sent back to host server 800 over the Internet 840.

In step 912, host server 800 stores the person performance data it receives from client terminal 820.

In step 914, host server 800 analyzes the person performance data to reveal any visual perception deficiencies, and to determine the level of performance of the person's visual perception process. Software 808 provides instructions and data for processor 804 to carry out this analysis. This is done by comparing the person performance data to data collected from persons with "normal vision," i.e., based on generally acceptable levels of performance for each of the different aspects of the visual perception process; this helps gauge the person's level of performance. Processor 804 performs this comparison, using data related to that of a "normal observer," which is stored in data storage device 806.

In step 916, new VPT Session parameters are generated for use in the next VPT Session, based at least in part upon the person performance data received by host server 800, and upon the analysis conducted on the person performance data by processor 804. These new parameters again define specific VPT Images 100 and VPTs to further improve the person's visual perception ability based upon the person's level of performance.

Further particulars of the hardware illustrated in FIG. 16, and the operations of the flow chart of FIG. 17, as well as many variations and modifications, are more particularly described in the above-cited U.S. patent application Ser. No. 169609 filed Nov. 13, 2002, published Jun. 12, 2003 as U.S. Patent Application 2003/0109800, the contents of which are incorporated herein by reference.

FIG. 18 illustrates a preferred method of determining the selected VPT session. The flow chart illustrated in FIG. 18 is similar to the flow chart (FIG. 10) in the above-cited published U.S. patent application Ser. No. 169609, except that, before the initial evaluation has started (steps 950, 952), a determination is made as to the type of training glasses to be applied to the patient during the treatment (steps 954, 956). As described earlier, training glasses with reduced refraction for the respective eye are applied to the one or both eyes being treated, particularly when the eye condition being treated is myopia, with or without astigmatism. Thus, in order to keep the contrasts within the desired range, the patients would be provided with training glasses with reduced refractive correction.

As also described earlier, not only is the type of training glasses determined, but also the training eye is determined. During the treatment, eye swapping may be effected wherein the trained eye is changed to the left eye, the right eye, or both eyes. There is a logical dependency between the change of the training eye, the training glasses, and the spatial frequency. When the training eye is changed, the training glasses, as well as the spatial frequency, may also be changed.

The remaining operations illustrated in the flow chart of FIG. 18 are basically the same as described in the above-cited published Patent Application (FIG. 10).

Thus, as described therein, there are two forms of VPT sessions available: an evaluation phase to ascertain a person's visual perception ability, and a treatment phase to improve the person's visual perception. Accordingly, as shown in step 1000, the first step in selecting a VPT Session is to determine whether the person has undergone the evaluation phase. If an evaluation has not been completed, the next step in the process is to move on to step 1002. Otherwise, the flowchart will continue at step 1010.

Starting with the evaluation phase and step 1002, a person undergoes an evaluation to ascertain the condition of the person's visual perception process. This data allows generation of effective VPTs that target the person's visual perception deficiencies. It also allows for a baseline set of data to gauge whether the person's visual perception is improving over the course of a particular VPT Session and over time. The evaluation process can be performed as often as necessary or desired.

In step 1004, the user inputs and performance data from past VPT Sessions are analyzed. This data provides information that is useful for establishing parameters that select VPT Images 100 and VPT Sessions to use to evaluate the person's visual perception.

In step 1006, a VPT Session is selected from a first group of potential VPT Sessions. VPTs within each VPT Session are used to collect data from the person regarding different aspects of the person's visual perception process to detect the existence of any physical or neural defects.

In step 1008, once the VPT Session has been selected, parameters for the VPT Session are generated. These parameters define the VPT Images that are to be presented to the person, and in particular control the difficulty of the VPTs as well as other characteristics.

In step 1010, a treatment phase is initiated for improving various aspects of the visual perception process of a person and alleviate visual perception deficiencies. The flow of the treatment phase is almost identical to that of the evaluation phase. In step 1012, the user inputs from past VPT Sessions are analyzed. In step 1014, a VPT Session is selected from a second group of VPT Sessions. This second group of VPT Sessions is different than the group described for the evaluation phase. In step 1016, parameters are generated which again define the VPT Images that are to be presented to the person.

FIG. 19 is a flow chart illustrating the operations involved in the analysis of an evaluation session. Three such evaluation sessions are illustrated.

In the first evaluation session, a determination is made of the starting size/spatial frequency (step 1110), and of the starting exposure duration (step 1112). A determination is then made of any changes required in the refraction of the training glasses (step 1114). The foregoing operations are repeated if the data is not complete (step 1116).

In the second evaluation session, a determination is made of the main orientations order (step 1120), of the worse orientation slice (step 1122), and of any additional required orientations (step 1124). A determination is then made whether any changes are required in the refraction of the training glasses (1126). If the data is not complete, the foregoing operations are repeated (step 1128).

In the third evaluation session, any missing data is completed (step 1130), and a determination is made as to any additional required parameters (1132).

FIGS. 20 and 21 illustrate the operations involved in analyzing a treatment session. Thus, the first operations are to calculate the normalized achieved contrast (step 1200), the facilitation at each mask distance (step 1202), and the total and optimal range facilitation (step 1204). A determination is then made as to whether the normalized contrast is satisfactory (step 1206). If not, a determination is made as to whether the normalized contrast is within the desired funnel (step 1208), and if not, the refraction of the training glasses is appropriately increased or decreased (step 1210).

On the other hand, if in operation 1206 the normalized contrast was found to be satisfactory, a determine is made as to whether the facilitation and optimal facilitation are satisfactory (step 1212). If not, the same state is repeated (step 1214), but if so, the program proceeds to the next state (step 1216).

As seen in the flow chart of FIG. 21, after the foregoing operations have been performed in a treatment session, a determination is made as to whether the visual acuity has changed or whether the last orientation was done (step 1220). If not, the analysis is completed, but if so, the trained eye is re-determined based on the new visual acuity (step 1222), of any required changes in the refraction of the training glasses (step 12224), and of the state, i.e., spatial frequency, orientation, exposure (step 1226).

The foregoing operations are performed until the desired "contrast funnel" is achieved, i.e., the desired range of contrast levels a patient is expected to achieve in order to gain optimal visual improvement while undergoing the foregoing treatment Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences identified by their accession numbers mentioned in this specification are herein incorporated in their entirety by reference into the specification, to the same extent as if each individual publication, patent, patent application or sequence identified by their accession number was specifically and individually indicated to be incorporated herein by reference. In addition, citation or identification of any reference in this application shall not be construed as an admission that such reference is available as prior art to the present invention.

What is claimed is:

1. A method of improving the visual perception ability of a person with respect to a particular eye condition of at least one eye, comprising:
    in at least one evaluation session of an evaluation phase, displaying to the person a plurality of images selected to test the visual perception ability of the person with respect to at least one visual defect, and to elicit responses from the person indicative of the level of the person's visual perception ability with respect to said at least one visual defect;
    utilizing said responses to select another plurality of images designed to treat the person with respect to a detected visual defect and thereby to improve the visual perception ability of the person with respect to the detected visual defect;
    and in a treatment phase, applying to said at least one eye of the person, training glasses with reduced refraction for the respective eye; and
    displaying to the person said another plurality of images in at least one treatment session while said training glasses are applied to said at least one eye of the person, until the visual perception ability of the person has been improved with respect to said detected visual defect.

2. The method according to claim 1, wherein said treatment phase includes a plurality of treatment sessions in each of which are displayed to the person a plurality of images designed to elicit responses to be used for selecting the plurality of images in a subsequent treatment session such as to progressively improve the visual perception ability of the person with respect to the detected visual defect; and
    wherein, after each treatment session, the refraction of the training glasses is increased, decreased, or remain the same for the next treatment session as determined in order to progressively improve the visual perception ability of the person with respect to the detected visual defect.

3. The method according to claim 1, wherein each of said treatment sessions includes a plurality of visual perception tasks in each of which there is displayed to the person at least one image including stimuli designed to elicit a response useful for selecting at least one other image to be displayed in the subsequent visual perception task of the respective treatment session such as to progressively improve the visual perception ability of the person with respect to the detected defect; and
    wherein, after at least one treatment session, the refraction of the training glasses is increased or decreased for the next treatment session as determined in order to progressively improve the visual perception ability of the person with respect to the detected visual defect.

4. The method according to claim 3, wherein said visual perception tasks in at least some of said sessions in the treatment phase include spatial frequency changes in which the spatial frequency of the stimuli is changed;
    wherein the spatial frequency is changed starting with lower spatial frequencies and progressively moving to higher spatial frequencies; and
    wherein after at least one treatment session, the refraction of the training glasses is increased or decreased for the next treatment session as determined in order to progressively improve the visual perception ability of the person with respect to the detected visual defect.

5. The method according to claim 3, wherein the eye condition includes astigmatism characterized by a distortion area in an astigmatic zone; and wherein, in at least some of said treatment sessions in the treatment phase, the orientation of the stimuli are changed by progressing towards the distortion area in the astigmatic zone.

6. The method according to claim 3, wherein said treatment phase includes a sufficient number of treatment sessions to improve the person's contrast sensitivity function by the person achieving a desired range of contrast levels representing a desired contrast funnel.

7. The method according to claim 6, wherein after at least one treatment session, the refraction of the training glasses is increased, decreased, or remains the same for the next treatment session as determined in order to achieve the desired range of contrast levels representing a desired contrast funnel to progressively improve the visual perception ability of the person with respect to the detected visual defect.

8. The method according to claim 1, wherein said evaluation phase includes a plurality of evaluation sessions in each of which at least one plurality of images are displayed to the person to elicit responses, the responses of each evaluation session being utilized to select the plurality of images to be displayed in the next evaluation session; and
    wherein each of said evaluation sessions includes a plurality of visual perception tasks in each of which there is displayed to the person at least one image designed to elicit a response useful for selecting at least one other image to be displayed in the subsequent visual perception task of the respective evaluation session such as to progressively improve the evaluation of the visual perception ability of the person with respect to the detected defect.

9. The method according to claim 1, wherein said plurality of images in at least the treatment phase are images based on Gabor Functions.

10. The method according to claim 1, wherein said plurality of images are displayed in a client's terminal in both said evaluation phase and said treatment phase;
    and wherein said elicited responses are communicated to a remotely-located server and utilized to select said another plurality of images designed to treat the person with respect to the detected visual defect.

11. Apparatus for improving the visual perception ability of a person with respect to a particular eye condition of at least one eye, comprising:
    a display device for displaying images to the person;
    an input device for displaying images to the person;
    training glasses to be worn by the person and having a reduced refraction with respect to at least one eye of the person;

and a processor programmed such that:

in an evaluation phase, before said training glasses have been applied to the person, the processor controls said display device to display to the person a plurality of images selected to test the visual perception ability of the person with respect to at least one visual defect, and utilizes responses inputted by the person via said input device to select another plurality of images designed to improve the visual perception ability of the person with respect to a detected visual defect;

and in treatment phase, after said training glasses have been applied to the person, the processor controls said display device to display to the person said another plurality of images to thereby improve the visual perception ability of the person with respect to said detected visual defect.

12. The apparatus according to claim 11, wherein said treatment phase includes a plurality of treatment sessions in each of which said processor controls said display device to display a plurality of images designed to elicit responses from said person, which responses are used for selecting the plurality of images in a subsequent treatment session, such as to progressively improve the visual perception ability of the person with respect to the detected visual defect.

13. The apparatus according to claim 12, wherein the refraction of said training glasses is variable such that after each treatment session, the refraction may be increased, decreased, or permitted to remain the same for the next treatment session, as determined by said processor in order to progressively improve the visual perception ability of the person with respect to the detected visual defect.

14. The apparatus according to claim 13, wherein said processor is programmed to conrol said display device to display in each of said treatment sessions a plurality of visual perception tasks in each of which there is displayed to the person at least one image including stimuli designed to elicit response useful for selecting at least one other image to be displayed in the subsequent visual perception task of the respective treatment session, such as to progressively improve the visual perception ability of the person with respect to the detected defect.

15. The apparatus according to claim 14, wherein said processor is programmed to control such display devices to display said visual perception tasks in at least some of said sessions in the treatment phase to include spatial frequency changes in which the spatial frequency of said stimuli is changed.

16. The apparatus according to claim 15, wherein said processor is programmed to control said display device to change the spatial frequency of said stimuli by starting with lower spatial frequencies and progressively moving to higher spatial frequencies.

17. The apparatus according to claim 14, wherein said processor is programmed to control said display device, in at least some of said treatment sessions in the treatment phase, to change the orientations of said stimuli by progressing them towards a distortion area in an astigmatic zone of the eye of treatment an eye for astigmatism.

18. The apparatus according to claim 14, wherein said processor is programmed to include in said treatment phase a sufficient number of treatment sessions to improve the person's contrast sensitivity function by the person achieving a desired range of contrast levels representing a desired contrast funnel.

19. The apparatus according to claim 12, wherein said evaluation phase includes a plurality of evaluation sessions in each of which said processor controls said display device to display a plurality of images to elicit responses inputted via said input device and utilized by said processor to select the plurality of images to be displayed in the next evaluation session.

20. The apparatus according to claim 11, wherein:

said display device and said input device are in a client terminal at the location of the person whose visual perception ability is to be improved;

said processor is in a remotely-located server;

said plurality of images are displayed in said client terminal in both said evaluation phase and said treatment phase; and said inputted responses are communicated to said remotely-located server via said input device, are utilized by said server to select said another plurality of images designed to treat the person with respect to the detected visual defect, and are communicated to said server to said client terminal for display thereon at the location of the person whose visual perception ability is to be improved.

* * * * *